(12) United States Patent
Easwaran et al.

(10) Patent No.: US 11,584,825 B2
(45) Date of Patent: Feb. 21, 2023

(54) POLYMER DYE MODIFICATION AND APPLICATIONS

(71) Applicant: Beckman Coulter, Inc., Brea, CA (US)

(72) Inventors: Arunkumar Easwaran, Miami, FL (US); Sergei Gulnik, Miami, FL (US); Massimiliano Tomasulo, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 484 days.

(21) Appl. No.: 16/711,131

(22) Filed: Dec. 11, 2019

(65) Prior Publication Data
US 2020/0190253 A1 Jun. 18, 2020

Related U.S. Application Data

(60) Provisional application No. 62/780,119, filed on Dec. 14, 2018.

(51) Int. Cl.
C08G 61/10 (2006.01)
C09B 69/10 (2006.01)
G01N 33/533 (2006.01)
G01N 33/542 (2006.01)
(Continued)

(52) U.S. Cl.
CPC ............ C08G 61/10 (2013.01); C09B 69/105 (2013.01); G01N 33/533 (2013.01); G01N 33/542 (2013.01); G01N 33/545 (2013.01); G01N 33/582 (2013.01); C08G 2261/11 (2013.01); C08G 2261/145 (2013.01); C08G 2261/1424 (2013.01); C08G 2261/1432 (2013.01); C08G 2261/1644 (2013.01); C08G 2261/18 (2013.01); C08G 2261/228 (2013.01); C08G 2261/314 (2013.01); C08G 2261/78 (2013.01); C08G 2261/94 (2013.01)

(58) Field of Classification Search
CPC ......... C08G 75/32; C08G 75/02; H01L 51/30; H01L 51/26; H01L 51/558; H01L 51/36
See application file for complete search history.

(56) References Cited

U.S. PATENT DOCUMENTS 4,486,530 A   12/1984   David et al.
4,703,004 A   10/1987   Hopp et al.
5,187,288 A   2/1993    Kang et al.
(Continued)

FOREIGN PATENT DOCUMENTS

AU   2017250778   11/2018
BR   112018071026   2/2019
(Continued)

OTHER PUBLICATIONS

"U.S. Appl. No. 16/092,180, Response filed Nov. 10, 2020 to Restriction Requirement dated Sep. 10, 2020", 17 pgs.
(Continued)

Primary Examiner — Shane Fang
(74) Attorney, Agent, or Firm — Merchant & Gould, P.C.

(57) ABSTRACT

Water-soluble photoactive polymers, included polymer tandem dyes, as described as well as methods for their preparation and use. The photoactive polymers can be prepared by direct modification of core polymers (e.g., violet excitable polymers) with dyes or other functional groups. Methods of detecting analytes using the polymers are also described.

15 Claims, 2 Drawing Sheets

(51) Int. Cl.
  *G01N 33/545* (2006.01)
  *G01N 33/58* (2006.01)

(56) References Cited

U.S. PATENT DOCUMENTS

| | | | |
|---|---|---|---|
| 5,573,909 | A | 11/1996 | Singer et al. |
| 5,576,424 | A | 11/1996 | Mao et al. |
| 5,582,977 | A | 12/1996 | Yue et al. |
| 5,656,449 | A | 8/1997 | Yue |
| 5,658,751 | A | 8/1997 | Yue et al. |
| 5,696,157 | A | 12/1997 | Wang et al. |
| 5,723,218 | A | 3/1998 | Haugland et al. |
| 5,798,276 | A | 8/1998 | Haugland et al. |
| 5,846,737 | A | 12/1998 | Kang |
| 5,863,753 | A | 1/1999 | Haugland et al. |
| 6,004,536 | A | 12/1999 | Leung et al. |
| 6,005,113 | A | 12/1999 | Wu et al. |
| 6,130,101 | A | 10/2000 | Mao et al. |
| 6,162,931 | A | 12/2000 | Gee et al. |
| 6,316,267 | B1 | 11/2001 | Bhalgat et al. |
| 6,399,392 | B1 | 6/2002 | Haugland et al. |
| 6,562,632 | B1 | 5/2003 | Szalecki et al. |
| 6,579,718 | B1 | 6/2003 | Yue et al. |
| 6,716,979 | B2 | 4/2004 | Diwu et al. |
| 6,972,326 | B2 | 12/2005 | Haugland et al. |
| 7,144,950 | B2 | 12/2006 | Bazan et al. |
| 7,446,202 | B2 | 11/2008 | Dallwig et al. |
| 7,462,683 | B2 | 12/2008 | Yamamoto et al. |
| 7,666,392 | B2 | 2/2010 | Kolb et al. |
| 7,671,214 | B2 | 3/2010 | Leung et al. |
| 7,687,282 | B2 | 3/2010 | Tsien et al. |
| 7,723,455 | B2 | 5/2010 | Becker et al. |
| 7,855,275 | B2 | 12/2010 | Eigenbrot et al. |
| 8,309,300 | B2 | 11/2012 | Junutula et al. |
| 8,362,193 | B2 | 1/2013 | Gaylord et al. |
| 8,455,613 | B2 | 6/2013 | Gaylord et al. |
| 8,575,303 | B2 | 11/2013 | Gaylord et al. |
| 9,000,130 | B2 | 4/2015 | Bhakta et al. |
| 9,139,869 | B2 | 9/2015 | Gaylord et al. |
| 9,547,008 | B2 | 1/2017 | Gaylord et al. |
| 9,896,538 | B2 | 2/2018 | Diwu et al. |
| 10,094,838 | B2 | 10/2018 | Gaylord et al. |
| 10,288,620 | B2 | 5/2019 | Gaylord et al. |
| 10,302,648 | B2 | 5/2019 | Gaylord et al. |
| 10,365,285 | B2 | 7/2019 | Gaylord et al. |
| 10,458,989 | B2 | 10/2019 | Gaylord et al. |
| 10,641,775 | B2 | 5/2020 | Gaylord et al. |
| 10,955,417 | B2 | 3/2021 | Gaylord et al. |
| 10,962,546 | B2 | 3/2021 | Gaylord et al. |
| 2004/0101909 | A1 | 5/2004 | Lemieux et al. |
| 2005/0059168 | A1 | 3/2005 | Bazan et al. |
| 2006/0183140 | A1 | 8/2006 | Bazan et al. |
| 2007/0060736 | A1 | 3/2007 | Becker et al. |
| 2010/0150942 | A1 | 6/2010 | Cantor |
| 2010/0227974 | A1 | 9/2010 | Schulte et al. |
| 2011/0095280 | A1 | 4/2011 | Meyer et al. |
| 2011/0256549 | A1* | 10/2011 | Gaylord ............. C09K 11/06 |
| | | | 562/466 |
| 2012/0252986 | A1 | 10/2012 | Liu et al. |
| 2013/0011388 | A1 | 1/2013 | Nur et al. |
| 2013/0027636 | A1 | 1/2013 | Marrocco, III et al. |
| 2013/0108619 | A1 | 5/2013 | Melamed |
| 2013/0177574 | A1 | 7/2013 | Ravindranath et al. |
| 2014/0357898 | A1 | 12/2014 | Kawano et al. |
| 2016/0264737 | A1* | 9/2016 | Bartholomew ...... G01N 33/582 |
| 2016/0266131 | A1* | 9/2016 | Liang ............. G01N 33/582 |
| 2019/0144601 | A1 | 5/2019 | Easwaran et al. |

FOREIGN PATENT DOCUMENTS

| | | |
|---|---|---|
| BR | 102019025989 A2 | 6/2020 |
| CA | 3020926 | 10/2017 |
| CN | 101553579 | 10/2009 |
| CN | 103328532 | 9/2013 |
| CN | 109415623 | 3/2019 |
| CN | 111320744 A | 6/2020 |
| EP | 1717258 A1 | 11/2006 |
| EP | 3443049 | 2/2019 |
| EP | 3670609 | 6/2020 |
| EP | 3443049 | 4/2021 |
| JP | 2008519140 | 6/2008 |
| JP | 2010501030 | 1/2010 |
| JP | 2010503685 | 2/2010 |
| JP | 2010540885 | 12/2010 |
| JP | 2011500916 | 1/2011 |
| JP | 2013517374 | 5/2013 |
| JP | 2019519623 | 7/2019 |
| JP | 2020109162 A | 7/2020 |
| JP | 2021102779 | 7/2021 |
| JP | 2021165407 | 10/2021 |
| KR | 20180132750 | 12/2018 |
| WO | WO-2005014689 A2 | 2/2005 |
| WO | 2005100437 | 10/2005 |
| WO | 2008100344 | 8/2008 |
| WO | 2009051560 | 4/2009 |
| WO | 2010151807 | 12/2010 |
| WO | 2011091086 | 7/2011 |
| WO | 2016019929 | 2/2016 |
| WO | WO-2016144653 A1 | 9/2016 |
| WO | 2017180998 | 10/2017 |
| WO | 2017180998 | 12/2017 |

OTHER PUBLICATIONS

"U.S. Appl. No. 16/092,180, Restriction Requirement dated Sep. 10, 2020", 7 pgs.

"Australian Application Serial No. 2017250778, First Examination Report dated Oct. 9, 2020", 4 pgs.

"Brazilian Application Serial No. 1120180710261, Voluntary Amendment filed Apr. 8, 2020", w/English claims, 36 pgs.

"European Application Serial No. 19216268.3, Extended European Search Report dated May 26, 2020", 7 pgs.

"European Application Serial No. 19216268.3, Response filed Dec. 18, 2020 to Extended European Search Report dated May 26, 2020", 15 pgs.

"Indian Application Serial No. 201847039964, First Examination Report dated Jul. 7, 2020", w/English Translation, 6 pgs.

"Indian Application Serial No. 201847039964, Response filed Dec. 24, 2020 to First Examination Report dated Jul. 7, 2020", 44 pgs.

"Becton Dickinson Filed a Case Against Beckman Coulter Over Alleged Patent Infringement", MaxVal, [Online] Retrieved from the Internet: URL: https: www.maxval.com blog becton-dickinson-filed-a-case-against-beckman-coulter-over-alleged-patent-infringement , [Retrieved on Sep. 29, 2021], (Jul. 1, 2021), 6 pgs.

"Japanese Application Serial No. 2018-554032, Response filed Apr. 2, 2021 to Office Action dated Jan. 15, 2021", with English translation, 56 pages.

"Japanese Application Serial No. 2018-554032, Decision to Grant a Patent dated Apr. 26, 2021", with English Translation and Allowed Claims, 22 pages.

"European Application Serial No. 17737077.2, Intention to Grant a European Patent dated Mar. 18, 2021", with Allowed Claims, 12 pages.

"Australian Application Serial No. 2017250778, Response filed Aug. 4, 2021 to First Examination Report dated Oct. 9, 2021", 35 pgs.

"Brazilian Application Serial No. 1120180710261, Office Action dated Aug. 13, 2021", with English claims, 80 pages.

"Chinese Application Serial No. 201780031306.5, Response filed Aug. 17, 2021 to Office Action dated May 8, 2021", with Concise Statement of Relevance, 48 pages.

"Korean Application Serial No. 10-2018-7031258, Notice of Allowance dated Aug. 23, 2021", with English translation, 4 pages.

"U.S. Appl. No. 16/092,180, Notice of Allowance dated Oct. 18, 2021", 5 pgs.

"European Application Serial No. 21156248.3, Extended European Search Report dated Oct. 8, 2021", 5 pgs.

An, Lingling, "A Fluorescence Ratiometric Protein Assay Using Light-Harvesting Conjugated Polymers", Macromol. Rapid Commun. 2006, 27, (2006), 993-997.

(56) References Cited

OTHER PUBLICATIONS

An, Lingling, "Cationic conjugated polymers for homogeneous and sensitive fluorescence detection of hyaluronidase", Sci China Ser B-Chem, 52(6), (Jun. 2009), 827-832.

Bernius, Mark T, "Progress with Light-Emitting Polymers", Adv. Mater. 2000, 12(23), (Dec. 1, 2000), 1737-1750.

Burrows, Hugh D, "Aqueous Solution Behavior of Anionic Fluorene-co-thiophene-Based Conjugated Polyelectrolytes", Applied Materials and Interfaces, 1(4), (2009), 864-874.

Feng, Fude, "Water-Soluble Conjugated Polymers for Fluorescent-Enzyme Assays", Macromol. Rapid Commun. 2010, 31, (2010), 1405-1421.

Gaylord, Brent, "DNA Hybridization Detection with Water-Soluble Conjugated Polymers and Chromophore-Labeled Single-Stranded DNA", J. Am. Chem. Soc., 125(4), (2003), 896-900.

Gaylord, Brent S, "DNA detection using water-soluble conjugated polymers and peptide nucleic acid probes", PNAS, 99(17), (2002), 10954-10957.

Gaylord, Brent S, "SNP detection using peptide nucleic acid probes and conjugated polymers: Applications in neurodegenerative disease identification", PNAS, 102(1), (Jan. 4, 2005), 34-39.

Hou, Qiong, "Novel red-emitting fluorene-based copolymers", J. Mater. Chem., 2002, 12, (2002), 2887-2892.

Inbasekaran, Michael, "Fluorene homopolymersand copolymers", Synthetic Metals 111-112, (2000), 397-401.

Lee, Kangwon, "Sensitive and Selective Label-Free DNA Detection by Conjugated Polymer-Based Microarrays and Intercalating Dye", Chem. Mater. 2008, 20(9), (2008), 2848-2850.

Li, Kai, "Generic Strategy of Preparing Fluorescent Conjugated-Polymer-Loaded Poly(DL-lactide-co-Glycolide) Nanoparticles for Targeted Cell Imaging", Adv. Funct. Mater. 2009, 19, (2009), 3535-3542.

Li, Kai, "Water-soluble conjugated polymers as the platform for protein sensors", Polym. Chem., 2010, 1,, (2010), 252-259.

Liu, Bin, "Synthesis of a novel cationic water-soluble efficient blue photoluminescent conjugated polymer", Chem. Commun., 2000, (2000), 551-552.

Liu, Bin, "Synthesis of cationic conjugated polymers for use in label-free DNA microarrays", Nature Protocols, 1(4), (2006), 1698-1702.

Pei, Qibing, "Efficient Photoluminescence and Electroluminescence from a Soluble Polyfluorene", J. Am. Chem. Soc. 1996, 118, (1996), 7416-7417.

Pu, Fang, "Universal Platform for Sensitive and Label-Free Nuclease Assay Based on Conjugated Polymer and DNA Intercalating Dye Complex", Langmuir 2010, 26(6), (2010), 4540-4545.

Shi, Jianbing, "Synthesis and Characterization of Water-Soluble Conjugated Glycopolymer for Fluorescent Sensing of Concanavalin A", Chem. Asian J. 2010, 5, (2010), 301-308.

Stork, Martin, "Energy Transfer in Mixtures of Water-Soluble Oligomers: Effect of Charge, Aggregation, and Surfactant Complexation", Adv. Mater. 2002, 14(5), (Mar. 4, 2002), 361-366.

Sun, Chengjun, "Application of cationic conjugated polymers in microarrays using label-free DNA targets", Nature Protocols, 2(9), (2007), 2148-2151.

Wang, Shu, "Fluorescein Provides a Resonance Gate for FRET from Conjugated Polymers to DNA Intercalated Dyes", J. Am. Chem. Soc., 126(17), (2004), 5446-5451.

Xue, Cuihua, "Highly Water-Soluble, Fluorescent, Conjugated Fluorene-Based Glycopolymers with Poly(ethylene glycol)-Tethered Spacers for Sensitive Detection of *Escherichia coli*", Chem. Eur. J. 2009, 15, (2009), 2289-2295.

Xue, Cuihua, "Facile, Versatile Prepolymerization and Postpolymerization Functionalization Approaches for Well-Defined Fluorescent Conjugated Fluorene-Based Glycopolymers", Macromolecules 2006, 39, (2006), 5747-5752.

Yamamoto, T, "Synthesis of soluble poly(9,10-dihydrophenanthrene-2,7-diyl)s.A new class of luminescent poly(p-phenylene)s with ethylene type bridges", Polymer, Elsevier Science Publishers B.V, GB, vol. 45, No. 24, (Nov. 1, 2004), 8085-8089.

U.S. Appl. No. 16/092,180, filed Oct. 8, 2018, Photoactive Macromolecules and Uses Thereof.

"International Application Serial No. PCT/US2017/027611, International Search Report dated Dec. 7, 2017", 5 pgs.

"International Application Serial No. PCT/US2017/027611, Written Opinion dated Dec. 7, 2017", 8 pgs.

"International Application Serial No. PCT/US2017/027611, International Preliminary Report on Patentability dated Oct. 25, 2018", 10 pgs.

"International Application Serial No. PCT/US2017/027611, Invitation to Pay Add'l Fees and Partial Search Report dated Oct. 11, 2017", 9 pgs.

"European Application Serial No. 17737077.2, Response filed May 23, 2019 to Communication pursuant to Rules 161(1) and 162 EPC dated Nov. 22, 2018", 29 pgs.

Yamamoto, "Conjugated Polymers Consisting of 9,10-Dihydrophenanthrene Units", Macromol. Chern. Phys. vol. 212, (2011), 2406-2416.

"Brazilian Application Serial No. 1120180710261, Office Action dated Jun. 1, 2021", w/ English Machine Translation, 10 pgs.

"Korean Application Serial No. 10-2018-7031258, Response filed May 11, 2021 to Notice of Preliminary Rejection dated Mar. 11, 2021", w/ English claims, 64 pgs.

"Australian Application Serial No. 2019280076, First Examination Report dated Jun. 18, 2021", 3 pgs.

"U.S. Appl. No. 16/092,180, Response filed Jun. 30, 2021 to Final Office Action dated Apr. 30, 2021", 19 pgs.

"U.S. Appl. No. 16/092,180 Final Office Action Response filed Jun. 30, 2021", 20 pgs.

"U.S. Appl. No. 16/092,180, Notice of Allowance dated Jul. 21, 2021", 7 pgs.

"Japanese Application Serial No. 2021-63576, Voluntary Amendment filed Jul. 14, 2021", w/ English claims, 24 pgs.

"Indian Application Serial No. 201847039964, Hearing Notice dated Jan. 1, 2021", 2 pgs.

"Japanese Application Serial No. 2018-554032, Notification of Reasons for Rejection dated Jan. 15, 2021", w/ English Translation, 9 pgs.

"Korean Application Serial No. 10-2018-7031258, Notice of Preliminary Rejection dated Mar. 11, 2021", w/ English Translation, 17 pgs.

"U.S. Appl. No. 16/092,180, Response filed Apr. 21, 2021 to Non Final Office Action dated Jan. 21, 2021", 18 pgs.

"U.S. Appl. No. 16/092,180, Final Office Action dated Apr. 30, 2021", 7 pgs.

"European Application Serial No. 21156248.3, Response to Rule 58 filed Apr. 28, 2021", 12 pgs.

"Chinese Application Serial No. 201780031306.5, Office Action dated May 8, 2021", w/ English Translation, 32 pgs.

Chen, Yi, "Water-Soluble Anionic Conjugated Polymers for Metal Ion Sensing: Effect of Interchain Aggregation", Journal of Polymer Science, Part A: Polymer Chemistry, 47(19), (2009), 5057-5067.

* cited by examiner

POLYMER DYE MODIFICATION AND APPLICATIONS

CROSS-REFERENCE TO RELATED APPLICATION

This patent application claims the benefit of U.S. Provisional Patent Application No. 62/780,119, filed Dec. 14, 2018, entitled "POLYMER DYE MODIFICATION AND APPLICATIONS", which is incorporated by reference herein in its entirety.

BACKGROUND OF THE INVENTION

Water soluble fluorescent polymers can be used in a variety of biological applications by generating signals which can be monitored in real time and provide simple and rapid methods for the detection of biological targets and events. Water soluble fluorescent polymers are generally prepared by polymerizing monomers (e.g., violet excitable dihydrophenanthrene monomers) containing polyethylene glycol units for solubilizing the polymer. A general approach for the preparation of polymers with different colors/emission wavelengths involves the covalent attachment of acceptor dye molecules to a common polymeric backbone, allowing for efficient fluorescnence resonance energy transfer (FRET). These polymers are often referred to as "tandem polymer dyes."

The tandem polymer dye approach requires the introduction of an additional reactive monomer that carries one or more chemically modifiable functional groups for acceptor dye attachment. However, introducing new monomers presents a number of drawbacks. For example, extra synthetic steps are required for preparation of new monomers—which can be costly and time-consuming—and polymerization conditions need to be adjusted or entirely re-designed due to changes in monomer structure. Furthermore, replacing a monomer having a water-solubilizing group with a monomer for dye attachment can comprise the solubility of the desired product. See, e.g., U.S. Pat. Nos. 8,362,193 and 9,896,538. Considerable amounts of trial and error are necessary to identify the right combination and amounts of various monomers for preparing polymers with acceptable FRET properties and solubility levels.

BRIEF SUMMARY OF THE INVENTION

Provided herein are water-soluble photoactive polymers including conjugated polymers according to Formula I:

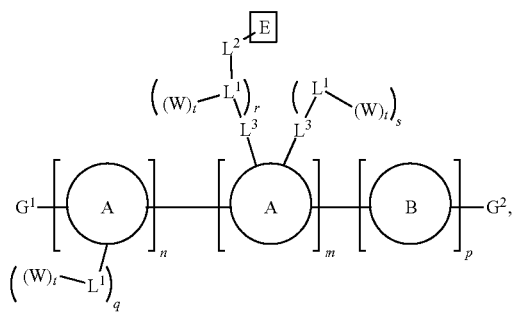

(I)

wherein:
each A is independently selected from the group consisting of an aromatic co-monomer and a heteroaromatic co-monomer;
$L^1$, $L^2$, and $L^3$ are linker moieties
W is a water-solubilizing moiety;
each E is an independently selected chromophore, functional moiety, or binding agent;
each B is independently selected from the group consisting of an aromatic co-monomer, a heteroaromatic co-monomer, a bandgap-modifying monomer, optionally substituted ethylene, and ethynylene;
$G^1$ and $G^2$ are independently selected from an unmodified polymer terminus and a modified polymer terminus;
subscripts n and m are independently integers ranging from 1 to 10,000,
subscript p is an integer ranging from 0 to 10,000, and the sum of subscripts n, m, and p ranges from 2 to 10,000;
subscript q is 1, 2, 3, or 4;
subscript r is 1, 2, 3, or 4;
subscript s is 0, 1, 2, or 3;
subscript t is 1 or 2
the sum of subscript r and s ranges from 1 to 4; and
A and B are distributed randomly or non-randomly in the conjugated polymer.

Some embodiments of the present disclosure provide a method of making a conjugated polymer according to Formula II:

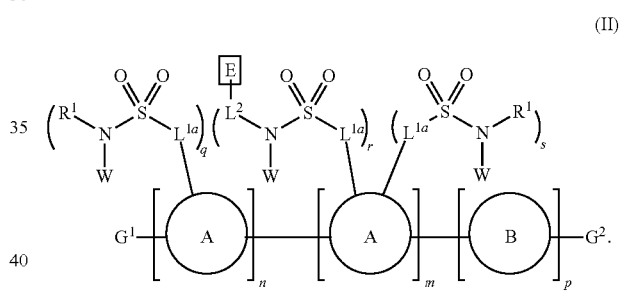

(II)

The method includes converting a conjugated polymer according to Formula IIa:

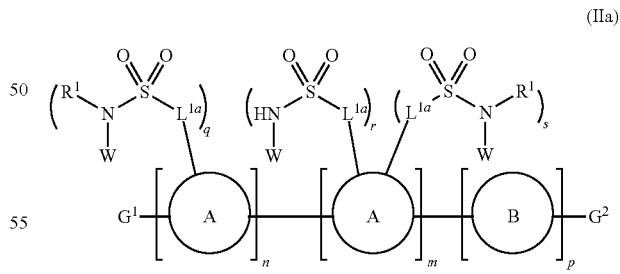

(IIa)

to the polymer according to Formula II, wherein:
A, B, $G^1$, $G^2$, $L^2$, W, E, and subscripts n, m, p, q, r, and s are as defined above;
$L^{1a}$ is a linker moiety; and
$R^1$ is selected from the group consisting of H and an amine protecting group.

Also provided are methods for detecting an analyte in a sample. The methods include providing a sample that is suspected of containing an analyte; and combining the sample with a conjugated polymer complex comprising a binding agent conjugated to a water soluble conjugated polymer as described herein. Assay techniques such as flow cytometry can be used to detect fluorescence associated with polymers bound to analytes of interest.

DETAILED DESCRIPTION OF THE INVENTION

Figure 1:
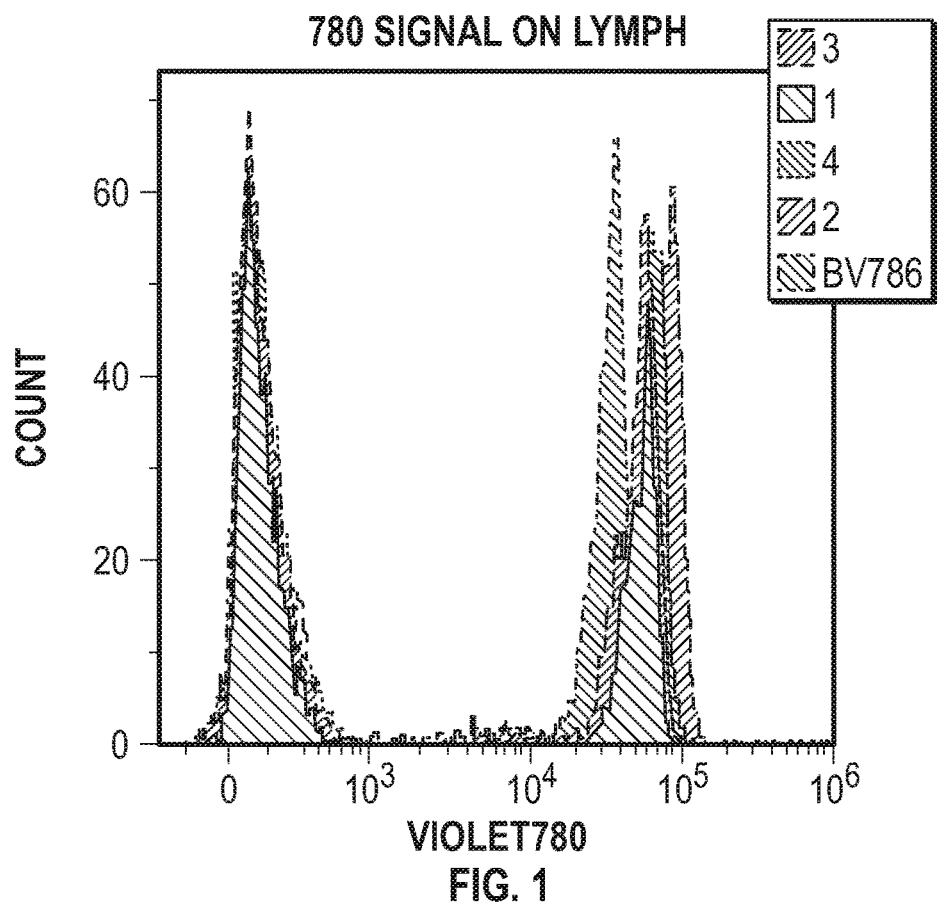
FIG. 1 shows an overlay of flow cytometry histograms generated using CD4 conjugated tandem polymer dye (5), including BV786.
Figure 2:
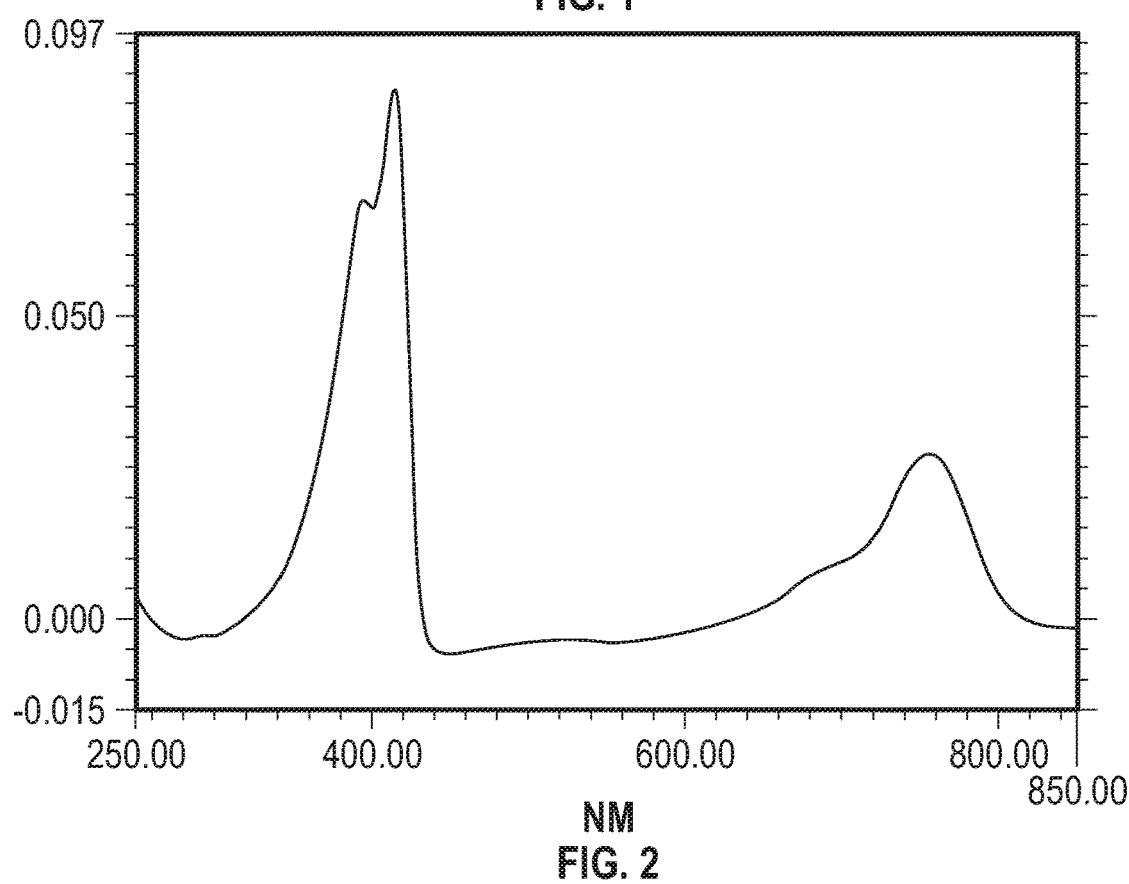
FIG. 2 shows the UV-vis absorbance spectrum of a sulfonamido(PEG) DHP polymer polymer-dye tandem containing Dy752 chromophores.
Figure 3:
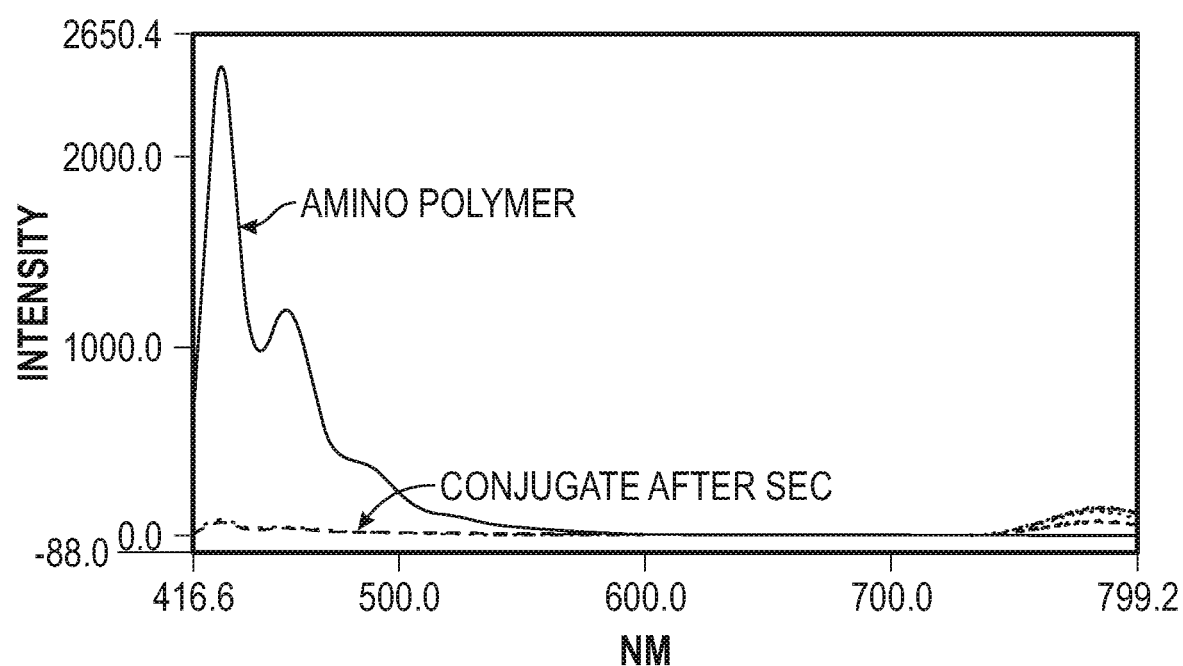
FIG. 3 shows the fluorescence emission spectrum of a CD4 mAb conjugated to a sulfonamido(PEG) DHP polymer polymer-dye tandem containing Dy752 chromophores. The tandem polymer showed a significant quenching effect at 450 nm due to the presence of the acceptor chromophores.

Provided herein are new polymer dyes which can be made via direct modification of core polymers (e.g., violet excitable polymers) with dyes or other functional groups. Dyes can be introduced by attaching them to functional groups already present in the polymer backbone, eliminating the need for an extra category of monomers to effect dye attachment. The starting polymer can be, for example, a violet polymer dye having a 9,10-dihydrophenanthrenedione (DHP) backbone with solubilizing polyethylene glycol (PEG) groups attached via sulfonamide bonds. Modification of the sulfonamide groups with dye molecules or other functional groups provides the new tandem polymer dyes.

The compositions and methods described herein provide a number of significant advantages. For example, only one polymer batch needs to be manufactured for violet polymers and violet tandem polymers. A common polymer platform can then be used to make the tandem polymers with any dye of choice, avoiding the requirement for new monomers. The overall composition of the polymer backbone will remain unaffected, and polymer solubility will remain satisfactory and easy to handle throughout synthesis and experimental use of the final products. In addition, the chemistry used for direct modification of the polymer backbone is itself quick and efficient.

I. Definitions

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. Unless otherwise specified, "substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the term "heteroalkyl," by itself or as part of another substituent, refers to an alkyl group of any suitable length and having from 1 to 3 heteroatoms such as N, O and S. For example, heteroalkyl can include ethers, thioethers and alkyl-amines. Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen atom of the alkyl group to form a hydroxy, thio or amino group. Alternatively, the heteroatom portion can be the connecting atom, or be inserted between two carbon atoms.

As used herein, the term "heteroalkylene" refers to a heteroalkyl group, as defined above, linking at least two other groups (i.e., a divalent heteroalkyl radical). The two moieties linked to the heteroalkylene group can be linked to the same atom or different atoms of the heteroalkylene group.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Unless otherwise specified, "substituted cycloalkyl" groups can be substituted with one or more groups selected from halo, hydroxy, amino, alkylamino, amido, acyl, nitro, cyano, and alkoxy. The term "lower cycloalkyl" refers to a cycloalkyl radical having from three to seven carbons including, for example, cyclopropyl, cyclobutyl, cyclopentyl, cyclohexyl, and cycloheptyl.

As used herein, the term "cycloalkylene" refers to a cycloalkyl group, as defined above, linking at least two other groups (i.e., a divalent cycloalkyl radical). The two moieties linked to the cycloalkylene group can be linked to the same atom or different atoms of the cycloalkylene group.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "haloalkoxy," by itself or as part of another substituent, refers to an alkoxy group where some or all of the hydrogen atoms are replaced with halogen atoms.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Unless otherwise specified, "substituted aryl" groups can be substituted with one or more groups selected from halo, hydroxy, amino, alkylamino, amido, acyl, nitro, cyano, and alkoxy.

As used herein, the term "arylene" refers to an aryl group, as defined above, linking at least two other groups (i.e., a divalent aryl radical).

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of heteroatoms can be included in the heteroaryl groups, such as 1, 2, 3, 4; or 5, or 1 to 2, 1 to 3, 1 to 4, 1 to 5, 2 to 3, 2 to 4, 2 to 5, 3 to 4, or 3 to 5. For example, heteroaryl groups can be $C_{5-8}$ heteroaryl, wherein 1 to 4 carbon ring atoms are replaced with heteroatoms; or $C_{5-8}$ heteroaryl, wherein 1 to 3 carbon ring atoms are replaced with heteroatoms; or $C_{5-6}$ heteroaryl, wherein 1 to 4 carbon ring atoms are replaced with heteroatoms; or $C_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, carbazole, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Unless otherwise specified, "substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the term "heteroarylene" refers to a heteroaryl group, as defined above, linking at least two other groups (i.e., a divalent heteroaryl radical).

As used herein the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. Unless otherwise specified, "substituted heterocyclyl" groups can be substituted with one or more groups selected from halo, hydroxy, amino, oxo (═O), alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "heterocyclylene" refers to a heterocyclyl group, as defined above, linking at least two other groups (i.e., a divalent heterocyclyl radical). The two moieties linked to the heterocyclylene group can be linked to the same atom or different atoms of the heterocyclylene group.

As used herein, the term "amine protecting group" refers to a chemical moiety that renders an amino group unreactive, but is also removable so as to restore the amino group. Examples of amine protecting groups include, but are not limited to, benzyloxycarbonyl; 9-fluorenylmethyloxycarbonyl (Fmoc); tert-butyloxycarbonyl (Boc); and allyloxycarbonyl (Alloc).

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_2$, wherein each R group is H or alkyl. An amino moiety can be ionized to form the corresponding ammonium cation.

As used herein, the term "sulfonyl" refers to a moiety —SO$_2$R, wherein the R group is alkyl, haloalkyl, or aryl.

The term "sulfonamide," as it pertains to linker moieties set forth herein, refers to a moiety —S(O)$_2$NR—, wherein the R group is H, alkyl, haloalkyl, or aryl. The term "sultam" refers to a cyclic sulfonamide (e.g., wherein the R group is bonded to the sulfur atom via an alkylene moiety).

The term "disulfonamide," as it pertains to linker moieties set forth herein, refers to a moiety —S(O)$_2$NRS(O)$_2$—, wherein the R group is H, alkyl, haloalkyl, or aryl.

The term "selenonamide," as it pertains to linker moieties set forth herein, refers to a moiety —Se(O)$_2$NR—, wherein the R group is H, alkyl, haloalkyl, or aryl.

The term "sulfinamide," as it pertains to linker moieties set forth herein, refers to a moiety —S(O)NR—, wherein the R group is H, alkyl, haloalkyl, or aryl.

The term "disulfinamide," as it pertains to linker moieties set forth herein, refers to a moiety —S(O)NRS(O)—, wherein the R group is H, alkyl, haloalkyl, or aryl.

The term "seleninamide," as it pertains to linker moieties set forth herein, refers to a moiety —Se(O)NR—, wherein the R group is H, alkyl, haloalkyl, or aryl.

The term "phosphonamide," as it pertains to linker moieties set forth herein, refers to a moiety —NR—PR(O)NR—, wherein each R group is independently H, alkyl, haloalkyl, or aryl.

The term "phosphinamide," as it pertains to linker moieties set forth herein, refers to a moiety —PR(O)NR—, wherein each R group is independently H, alkyl, haloalkyl, or aryl.

The term "phosphonamidate," as it pertains to linker moieties set forth herein, refers to a moiety —O—PR(O)NR—, wherein each R group is independently H, alkyl, haloalkyl, or aryl.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion. The term "carboxylate" as used herein refers to the conjugate base of a carboxylic acid, which generally can be represented by the formula —C(O)O—. For example, the term "magnesium carboxylate" refers to the magnesium salt of the carboxylic acid.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O═).

As used herein, the term "ammonium" refers to a cation having the formula NHR$_3^+$ where each R group, independently, is hydrogen or a substituted or unsubstituted alkyl, aryl, aralkyl, or alkoxy group. Preferably, each of the R groups is hydrogen.

As used herein, "oligoether" is understood to mean an oligomer containing structural repeat units having an ether functionality. As used herein, an "oligomer" is understood to mean a molecule that contains one or more identifiable structural repeat units of the same or different formula.

The term "sulfonate functional group" or "sulfonate," as used herein, refers to both the free sulfonate anion (—S(=O))$_2$O—) and salts thereof. Therefore, the term sulfonate encompasses sulfonate salts such as sodium, lithium, potassium and ammonium sulfonate.

The terms "polyethylene glycol" and "PEG" as used herein refer to the family of biocompatible water-solubilizing linear polymers based on the ethylene glycol monomer unit.

The term "carbamate" as used herein refers to the functional group having the structure —NR"CO$_2$R', where R' and R" are independently selected from hydrogen, ($C_1$-$C_8$) alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. Examples of carbamates include Boc, Fmoc, benzyloxycarbonyl, alloc, methyl carbamate, ethyl carbamate, 9-(2-sulfo)fluorenylmethyl carbamate, 9-(2,7-dibromo)fluorenylmethyl carbamate, Tbfmoc, Climoc, Bimoc, DBD-Tmoc, Bsmoc, Troc, Teoc, 2-phenylethyl carbamate, Adpoc, 2-chloroethyl carbamate, 1,1-dimethyl-2-haloethyl carbamate, DB-t-BOC, TCBOC, Bpoc, t-Bumeoc, Pyoc, Bnpeoc, and dimethylethyl carbamate.

The term "activated ester" as used herein refers to carboxyl-activating groups employed in peptide chemistry to promote facile condensation of a carboxyl group with a free amino group of an amino acid derivative. Descriptions of these carboxyl-activating groups are found in general textbooks of peptide chemistry; for example K. D. Kopple, "Peptides and Amino Acids", W. A. Benjamin, Inc., New York, 1966, pp. 50-51 and E. Schroder and K. Lubke, "The Peptides"; Vol. 1, Academic Press, New York, 1965, pp. 77-128.

The term "hydrazine" refers to a moiety having the structure —NHNH$_2$.

The term "aldehyde" as used herein refers to a chemical compound that has an —CHO group.

The term "thiol" as used herein refers to a compound that contains the functional group composed of a sulfur-hydrogen bond. The general chemical structure of the thiol functional group is R—SH, where R represents an alkyl, alkene, aryl, or other carbon-containing group of atoms.

The term "silyl" as used herein refers to Si(R$^z$)$_3$ wherein each R$^z$ independently is alkyl aryl or other carbon-containing group of atoms.

The term "diazonium salt" as used herein refers to a group of organic compounds with a structure of R—N$_2$$^+$X$^-$, wherein R can be any organic residue (e.g., alkyl or aryl) and X is an inorganic or organic anion (e.g., halogen).

The term "triflate" also referred to as trifluoromethanesulfonate, is a group with the formula CF$_3$SO$_3$.

The term "boronic acid" as used herein refers to a structure —B(OH)$_2$. It is recognized by those skilled in the art that a boronic acid may be present as a boronate ester at various stages of the synthetic steps disclosed herein; boronic acid is meant to include such esters. The term "boronic ester" or "boronate ester" as used herein refers to a chemical compound containing a —B(Z$^1$)(Z$^2$) moiety, wherein Z$^1$ and Z$^2$ together form a moiety where the atom attached to boron in each case is an oxygen atom. In some embodiments, the boronic ester moiety is a 5-membered ring. In some other embodiments, the boronic ester moiety is a 6-membered ring. In some other embodiments, the boronic ester moiety is a mixture of a 5-membered ring and a 6-membered ring.

II. Polymers

Provided herein are water-soluble conjugated polymers, including fluorescent polymers having monomer subunits such as dihydrophenanthrene (DHP), fluorene, and combinations thereof. Some embodiments of the present disclosure provide conjugated polymers according to Formula I:

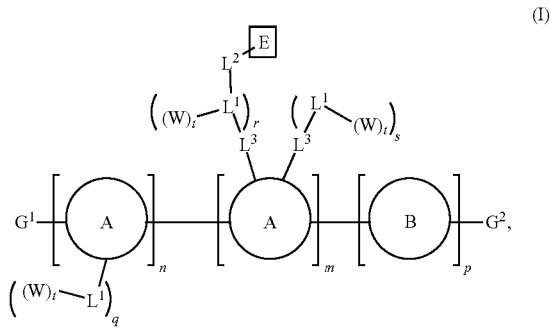

(I)

wherein:

each A is independently selected from the group consisting of an aromatic co-monomer and a heteroaromatic co-monomer;

L$^1$, L$^2$, and L$^3$ are linker moieties;

W is a water-solubilizing moiety;

each E is an independently selected chromophore, functional moiety, or binding agent;

each B is independently selected from the group consisting of an aromatic co-monomer, a heteroaromatic co-monomer, a bandgap-modifying monomer, optionally substituted ethylene, and ethynylene;

G$^1$ and G$^2$ are independently selected from an unmodified polymer terminus and a modified polymer terminus;

subscripts n and m are independently integers ranging from 1 to 10,000, subscript p is an integer ranging from 0 to 10,000, and the sum of subscripts n, m, and p ranges from 2 to 10,000;

subscript q is 1, 2, 3, or 4;

subscript r is 1, 2, 3, or 4;

subscript s is 0, 1, 2, or 3;

subscript t is 1 or 2 the sum of subscript r and s ranges from 1 to 4; and

A and B are distributed randomly or non-randomly in the conjugated polymer.

In some embodiments, L$^1$ comprises a sulfonamide, a sulfonamide, a sultam, a disulfinamide, an amide, a phosphonamide, a phosphonamidate, a phosphinamide or a secondary amine. In some embodiments, L$^1$ comprises a sulfonamide, an amide, a phosphonamide, or a secondary amine.

In some embodiments:

subscript q is equal to the sum of subscripts r and s, subscript r is 1 or 2, if subscript r is 1, then subscript s is 0 or 1, and if subscript r is 2, then subscript s is 0.

In some embodiments, each L$^3$ is a covalent bond.

In some embodiments, the conjugated polymer has a structure according to Formula II:

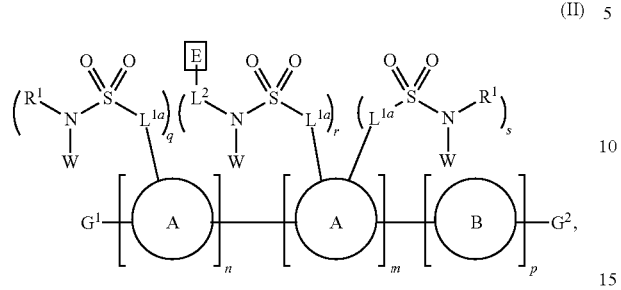

(II)

wherein:
$L^{1a}$ is a linker moiety; and
$R^1$ is selected from the group consisting of H and an amine protecting group.

A variety linkers $L^{1a}$ and $L^2$, as described herein, can be employed for synthesis of polymers according to Formula I and Formula II. In some embodiments:
- $L^{1a}$ is selected from the group consisting of a covalent bond, $C_{1-8}$ alkylene, 2- to 8-membered heteroalkylene (e.g., a divalent alkoxy linker), $C_{3-8}$ cycloalkylene, $C_{6-10}$ arylene, 5- to 12-membered heteroarylene, 5- to 12-membered heterocyclylene, —NHC(O)$L^a$—, —C(O)NH$L^a$—, —C(O)$L^a$—, and combinations thereof;
- $L^2$ is selected from the group consisting of a covalent bond, $C_{1-8}$ alkylene, 2- to 8-membered heteroalkylene (e.g., a divalent alkoxy linker), $C_{3-8}$ cycloalkylene, $C_{6-10}$ arylene, 5- to 12-membered heteroarylene, 5- to 12-membered heterocyclylene, —$L^b$NHC(O)—, —$L^b$C(O)NH—, —$L^b$C(O)—, —C(O)NH$L^b$—, —C(O)$L^b$—, and combinations thereof;
- $L^a$ and $L^b$ are independently selected from the group consisting of $C_{1-8}$ alkylene and 2- to 8-membered heteroalkylene; and
- $R^1$ is selected from the group consisting of H and an amine protecting group.

In some embodiments, polymers according to Formula II are provided wherein:
- $L^{1a}$ is selected from the group consisting of a covalent bond, $C_{1-8}$ alkylene, 2- to 8-membered heteroalkylene, —NHC(O)$L^a$—, —C(O)NH$L^a$—, and —C(O)$L^a$—,
- $L^2$ is selected from the group consisting of a covalent bond, $C_{1-8}$ alkylene; 2- to 8-membered heteroalkylene, —$L^b$NHC(O)—, —$L^b$C(O)NH—, —$L^b$C(O)—, —C(O)NH$L^b$—, and —C(O)$L^b$—;
- $L^a$ and $L^b$ are independently selected from the group consisting of $C_{1-8}$ alkylene and 2- to 8-membered heteroalkylene; and
- $R^1$ is selected from the group consisting of H and an amine protecting group.

In some embodiments, W comprises one or more ethylene glycol monomers. In some embodiments, W comprises poly(ethylene glycol).

In some embodiments, $L^3$ is a trivalent arylalkyl moiety having: a first point of attachment to a first $L^1$ moiety (or a first $L^{1a}$ moiety); a second point of attachment to a second $L^1$ moiety (or a second $L^{1a}$ moiety); and a third point of attachment to an A monomer. For example, some embodiments of the disclosure provide conjugated polymers having two or more chromophores attached as shown in Formula VI:

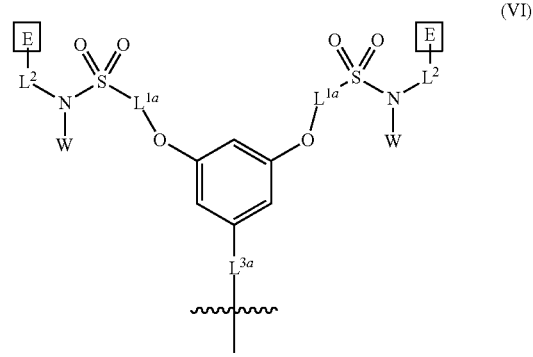

(VI)

wherein
$L^{3a}$ is selected from the group consisting of a covalent bond, $C_{1-8}$ alkylene, 2- to 8-membered heteroalkylene, —NHC(O)$L^a$—, —C(O)NHL$^a$—, and —C(O)$L^a$—;
$L^a$ and $L^b$ are independently selected from the group consisting of $C_{1-8}$ alkylene and 2- to 8-membered heteroalkylene;
and the wavy line is the point of the attachment to the a monomer.

In some embodiments, each A is the same co-monomer. In some embodiments, A is a fluorescent monomer. In some embodiments, A is a 9,10-phenanthrenedione-based monomer (e.g., a dihydrophenanthrene (DHP)-based monomer), a fluorene-based monomer, or a fluorenooxepine-based monomer. In some embodiments, "A" monomers in polymers according to Formula I are DHP-based monomers such as:

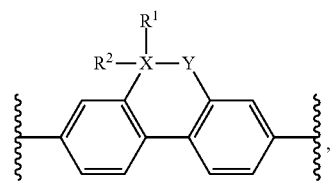

wherein:
each X is independently C or Si;
each Y is independently $CR^1R^2$ or $SiR^1R^2$;
each $R^1$ is independently an ammonium alkyl salt, an ammonium alkyloxy salt, an ammonium oligoether salt, a sulfonate alkyl salt, a sulfonate alkoxy salt, a sulfonate oligoether salt, a sulfonamido oligoether, or a moiety:

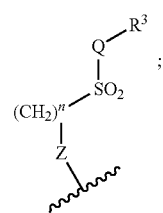

each $R^2$ is independently H, alkyl, alkenyl, alkynyl, cycloalkyl, haloalkyl, alkoxy, (hetero)aryloxy, aryl, (hetero)arylamino, a PEG group, an ammonium alkyl salt, an ammonium alkyloxy salt, an ammonium oligoether salt, a sulfonate alkyl salt, a sulfonate alkoxy salt, a sulfonate oligoether salt, a sulfonamido oligoether, or a moiety

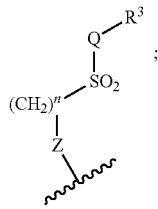

each $R^3$ is independently selected from the group consisting of H, alkyl, alkene, alkyne, cycloalkyl, haloalkyl, alkoxy, (hetero)aryloxy, aryl, (hetero)arylamino, and a PEG group;

each Z is independently selected from the group consisting of C, O, and N;

each Q is independently selected from the group consisting of a bond, NH, $NR^4$, and $CH_2$; and each subscript n is independently an integer from 0 to 20.

In some embodiments, $R^1$ is has the structure shown below, wherein Q is NH:

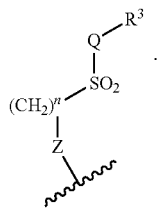

In some embodiments, the DHP-based monomer has a structure:

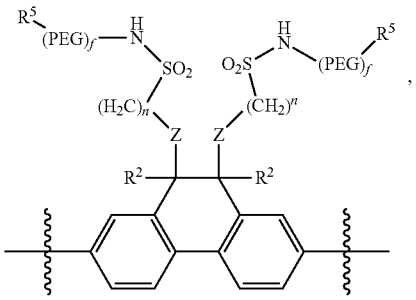

wherein:

each subscript f is independently an integer from 0 to 50, and each subscript n is independently an integer from 0 to 20, and each $R^5$ is independently H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ haloalkyl, $C_1$-$C_{20}$ alkoxy, $C_2$-$C_{26}$ aryloxy, $C_2$-$C_{26}$ heteroaryloxy, $C_2$-$C_{26}$ arylamino, or $C_2$-$C_{26}$ heteroarylamino.

In some embodiments, the DHP monomer has a structure:

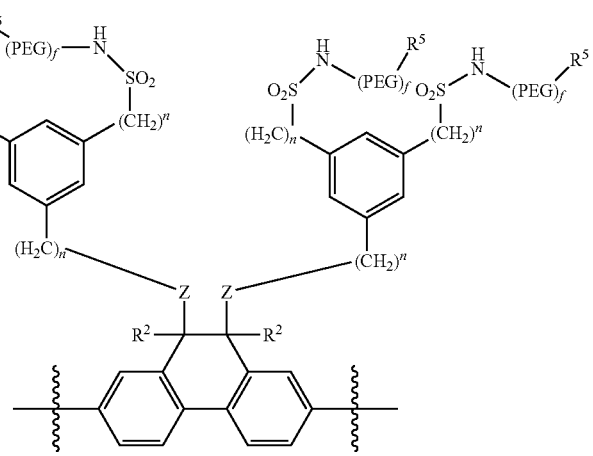

wherein:

each subscript f is independently an integer from 0 to 50, and each subscript n is independently an integer from 0 to 20, and each $R^5$ is independently H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ haloalkyl, $C_1$-$C_{20}$ alkoxy, $C_2$-$C_{26}$ aryloxy, $C_2$-$C_{26}$ heteroaryloxy, $C_2$-$C_{26}$ arylamino, or $C_2$-$C_{26}$ heteroarylamino.

In some embodiments, "A" monomers in polymers according to Formula I are fluorene-based monomers such as:

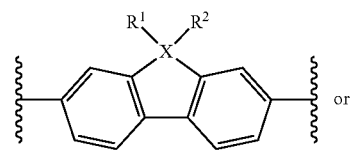

or

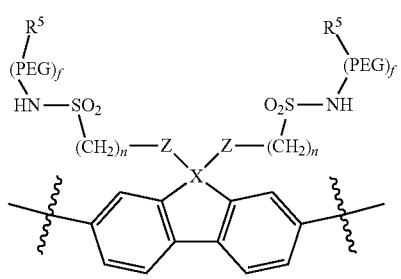

wherein X, Z, $R^1$, $R^2$, $R^5$, subscript n, subscript f are as defined above.

$R^1$ groups and $R^2$ groups such as ammonium alkyl salts, ammonium alkyloxy salts, ammonium oligoether salts, sulfonate alkyl salts, sulfonate alkoxy salts, sulfonate oligoether salts, sulfonamido oligoethers, or moieties having the structure:

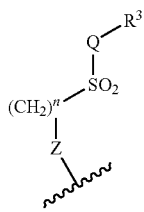

can impart solubility in water/buffer. In some embodiments, for example, the polymer is soluble at levels in excess of 10 mg/mL, in excess of 15 mg/mL, in excess of 20 mg/mL, in excess of 25 mg/mL, in excess of 30 mg/mL, in excess of 35 mg/mL, in excess of 40 mg/mL, in excess of 45 mg/mL, in excess of 50 mg/mL, in excess of 60 mg/mL, in excess of 70 mg/mL, in excess of 80 mg/mL, in excess of 90 mg/mL or in excess of 100 mg/mL.

In some embodiments, monomers of the present invention also include bridged monomers. For example, bridged monomers of the present invention include:

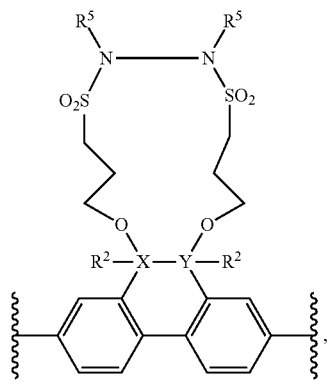

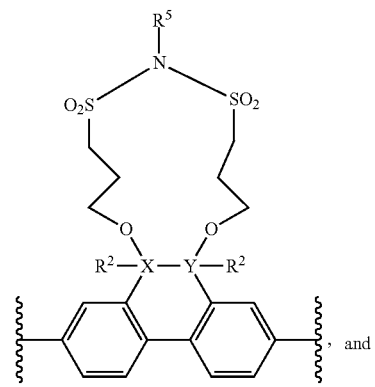

, and

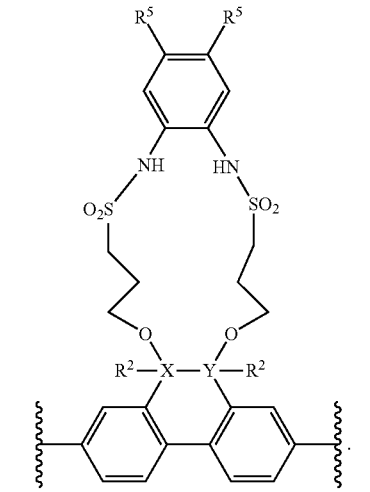

.

In some embodiments, "A" monomers in polymers according to Formula I are oxepine-based monomers (e.g., fluorenooxepine-based monomers), such as:

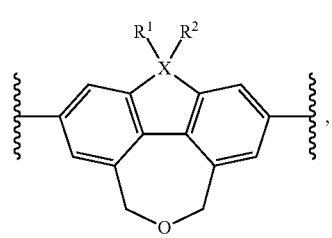

,

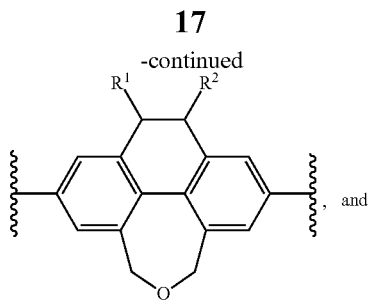

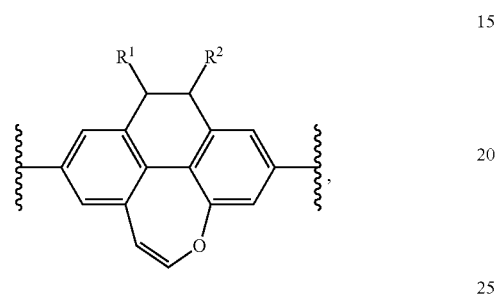

wherein X, $R^1$, and $R^2$ are as defined above.

Prior to polymerization, conducted according to methods including those described below, the terminal ends of the monomers are independently a halogen atom, a boronic ester or boronic an acid, a silyl group, a diazonium salt, a triflate group, an acetyloxy group, a sulfonate group, or phosphate which can undergo palladium- or nickel-catalyzed polymerization.

In some embodiments, the conjugated polymer has a structure according to Formula III:

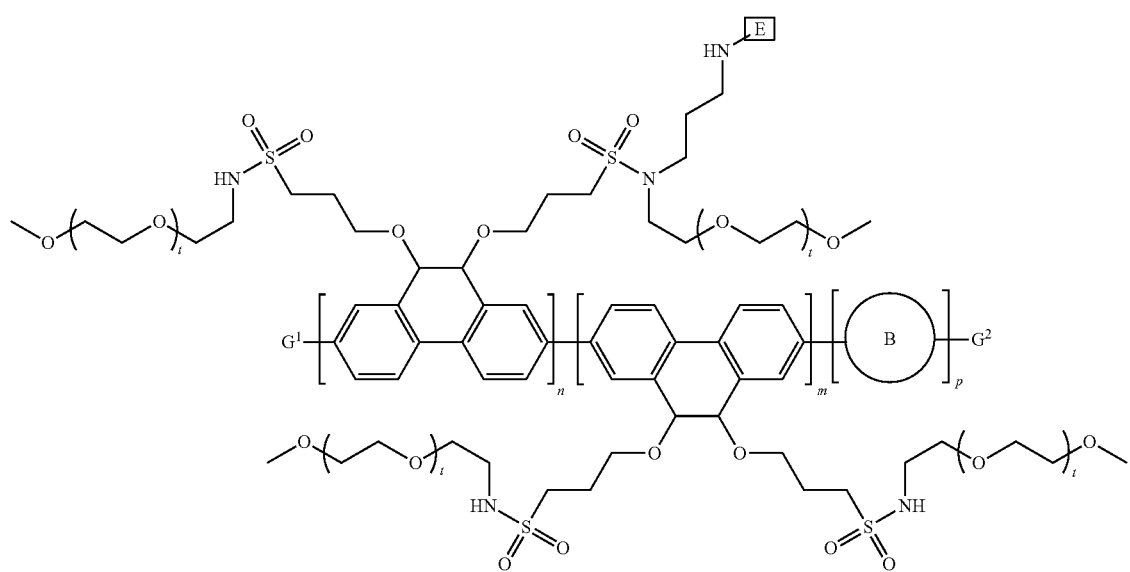

wherein each subscript t is an integer ranging from 1 to 20.

In some embodiments, "B" monomers of conjugated polymers according to Formula I are can alter the polymer band gap. Band gap altering monomers include structures such as:

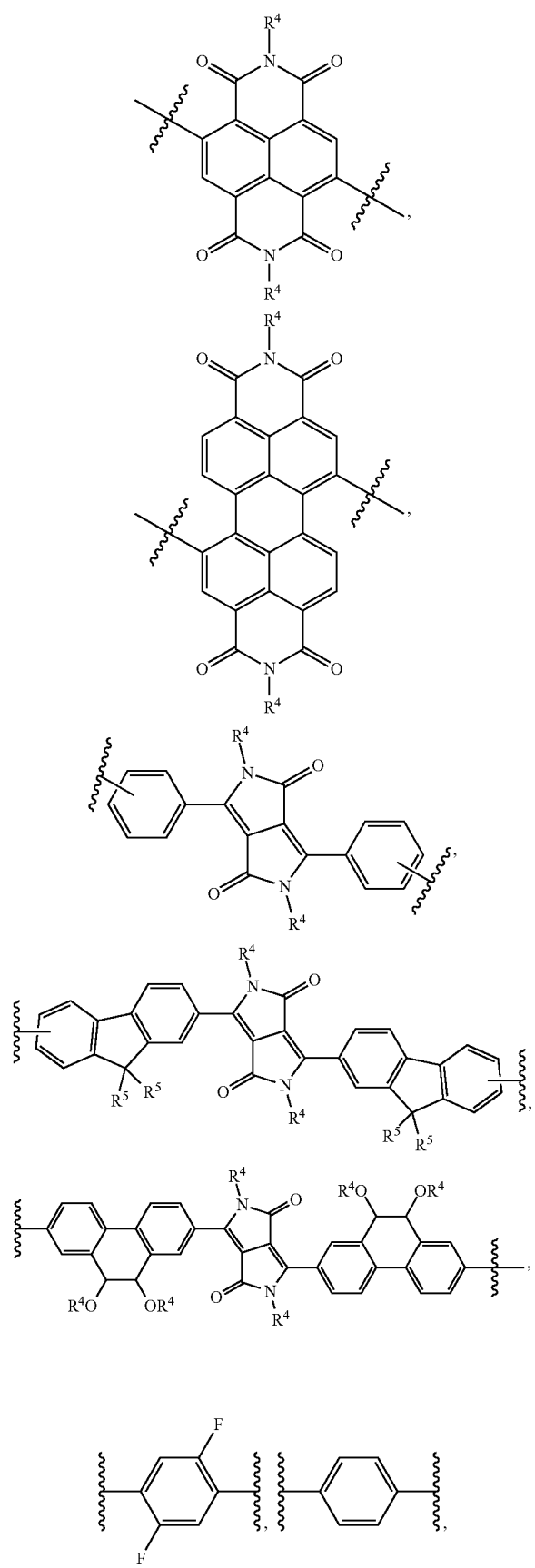

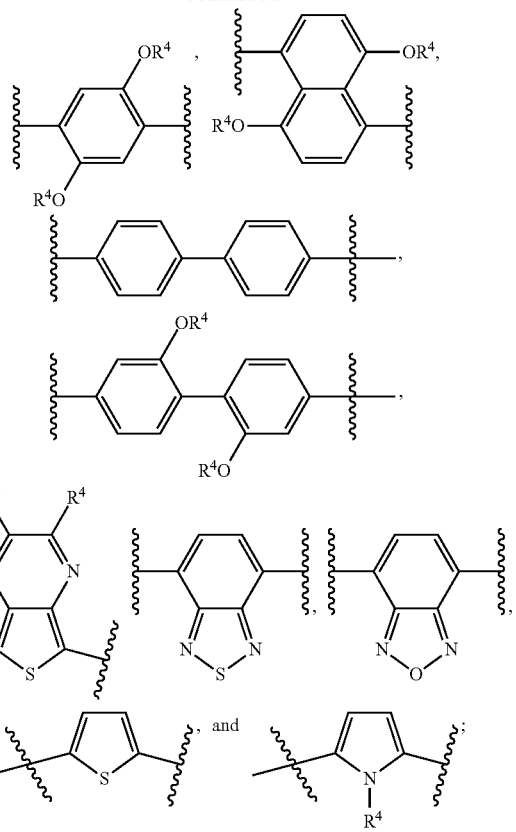

wherein:

each $R^4$ is independently H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ haloalkyl, $C_2$-$C_{26}$ aryl, $C_2$-$C_{26}$ heteroaryl, an ammonium alkyl salt, an ammonium alkyloxy salt, an ammonium oligoether salt, a sulfonate alkyl salt, a sulfonate alkoxy salt, a sulfonate oligoether salt, a sulfonamido oligoether, or $(CH_2)_x(OCH_2-CH_2)_yOCH_3$;

each $R^5$ is independently H, halogen, hydroxyl, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ haloalkyl, $C_1$-$C_{20}$ alkoxy, $C_2$-$C_{26}$ aryl, $C_2$-$C_{26}$ heteroaryl, $C_2$-$C_{26}$ aryloxy, $C_2$-$C_{26}$ heteroaryloxy, $C_2$-$C_{26}$ arylamino, $C_2$-$C_{26}$ heteroarylamino, an ammonium alkyl salt, an ammonium alkyloxy salt, an ammonium oligoether salt, a sulfonate alkyl salt, a sulfonate alkoxy salt, a sulfonate oligoether salt, a sulfonamido oligoether, or $(CH_2)_x(OCH_2-CH_2)_yOCH_3$ each x is independently an integer from 0-20; and each y is independently an integer from 0-50.

In some embodiments, "B" monomers of conjugated polymers are optionally substituted ethylene moieties, i.e., carbon-carbon double bonds having the formula —CR=CR—, wherein each R is independently H, alkyl, alkenyl, alkynyl, cycloalkyl, haloalkyl, alkoxy, (hetero)aryloxy, aryl, (hetero)arylamino, a PEG group, an ammonium alkyl salt, an ammonium alkyloxy salt, an ammonium oligoether salt, a sulfonate alkyl salt, a sulfonate alkoxy salt, a sulfonate oligoether salt, a sulfonamido oligoether, or a moiety

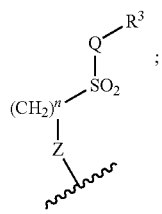

as defined above. In some embodiments, "B" monomers of conjugated polymers can include an ethynylene moieties, i.e., carbon-carbon triple bonds having the formula —C≡C—.

In some embodiments, one or both of $G^1$ and $G^2$ are modified with a capping moiety. In some embodiments, one of $G^1$ and $G^2$ is modified with a capping moiety, and one of $G^1$ and $G^2$ is modified with a reactive group for conjugation. Capping units $G^1$ and $G^2$ can be, for example, hydrogen, halogen, alkynyl, optionally substituted aryl (e.g., halogen-substituted aryl), optionally substituted heteroaryl, silyl, a diazonium salt, a triflate, an acetyloxy group, an azide, a sulfonate, a phosphate, a boronic acid-substituted aryl group, a boronic ester-substituted aryl group, a boronic ester, or a boronic acid. Capping units can also contain one or more a reactive group for conjugation (e.g., functional group such as an amine, a carbamate, a carboxylic acid, a carboxylate, a maleimide, an activated ester such as an N-hydroxysuccinimidyl ester, a hydrazine, an azide, an alkyne, an aldehyde, or a thiol), which can be covalently bonded to binding agents and substrate materials, as described in more detail below.

In some embodiments, polymers as described herein are characterized by a minimum number average molecular weight of greater than 5,000 g/mol, greater than 10,000 g/mol, greater than 15,000 g/mol, greater than 20,000 g/mol, greater than 25,000 g/mol, greater than 30,000 g/mol, greater than 40,000 g/mol, greater than 50,000 g/mol, greater than 60,000 g/mol, greater than 70,000 g/mol, greater than 80,000 g/mol, greater than 90,000 g/mol, or greater than 100,000 g/mol.

In some embodiments, polymers as described herein are characterized by a minimum weight average molecular weight of greater than 5,000 g/mol, greater than 10,000 g/mol, greater than 15,000 g/mol, greater than 20,000 g/mol, greater than 25,000 g/mol, greater than 30,000 g/mol, greater than 40,000 g/mol, greater than 50,000 g/mol, greater than 60,000 g/mol, greater than 70,000 g/mol, greater than 80,000 g/mol, greater than 90,000 g/mol, or greater than 100,000 g/mol. Number average and weight average molecular weight values can be determined by gel permeation chromatography (GPC) using polymeric standards (e.g., polystyrene or like material).

III. Methods for Polymer Preparation

Also provided herein are methods for preparing conjugated polymers.

A. Monomer Synthesis

DHP monomers of the present invention can be made as shown below.

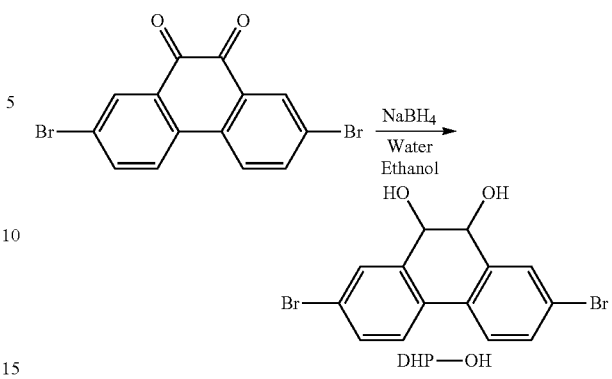

For example, 2,7-dibromo-trans-9,10-dihydrophenanthrene-9,10-diol (DHP—OH) can be prepared as follows. In a conical flask (2 L), about 26 g of NaBH$_4$ is added to a stirring water-ethanol mixture (1:6.5 v:v). To this solution, about 24 g of 2,7-dibromophenanthrene,9,10-dione is added portion-wise over a period of about 5 min. The reaction mixture is stirred for around 24 hours, and the color of the solution changes from orange red to pale yellow to white by the end of the reaction. The reaction is stopped and the reaction mixture is neutralized with dil HCl acid. After the neutralization, the white precipitate is filtered and washed with excess water. The isolated precipitate is was washed with very cold (<−15° C.) ethanol (100 mL) and methanol (100 mL).

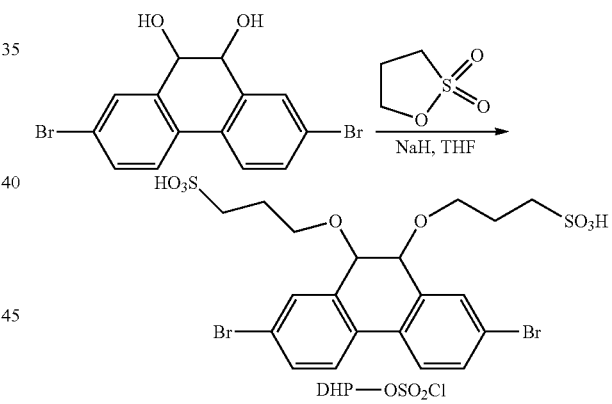

DHP—OSO$_3$H can be prepared as follows. In a 2 neck round bottom flask, DHP—OH (3.6 g) and 18-crown-6 (500 mg) are dissolved in 120 mL of THF. The solution is purged with nitrogen (20 min) and NaH (2 g) is added while nitrogen purging continues. The color of the solution changes from colorless to pale pink, dark pink, brown and dark green in 10-15 min. In another flask, 12 g of 1,3 propane sultone is dissolved in 20 ml of THF and nitrogen purged. This sultone solution is added to DHP—OH solution by addition funnel over a period of 20-30 min. The reaction is stirred at RT for 4-5 hrs. The solvents are evaporated, and the resulting solid material is dissolved in water. Acetone is added to obtain a white precipitate in the form of disodium salt. The precipitate is filtered and redissolved in water (minimal amount), neutralized with HCl, and precipitated again in acetone. Repeated precipitation (2-3 times) followed by centrifugation affords the product as a white solid.

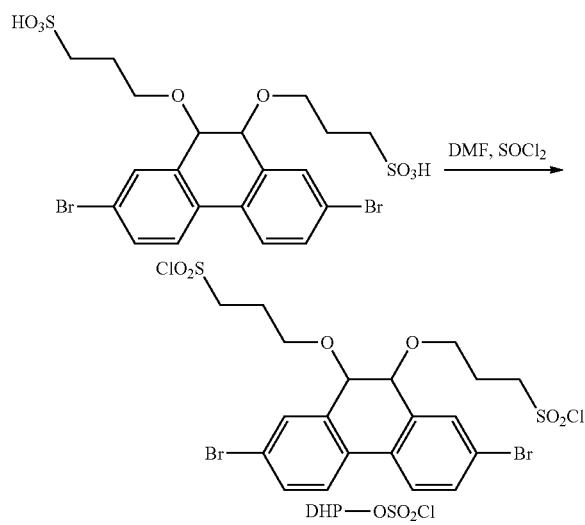

DHP—OSO$_2$Cl can be prepared as follows. 5 g of DHP—OSO$_3$H is measured into a round bottom flask and mixed with 25 mL of DMF. To this about 10 mL of SOCl$_2$ is added dropwise and the mixture is allowed to stir overnight. The reaction mixture is then poured into 200 mL water and the product precipitate is filtered and dried.

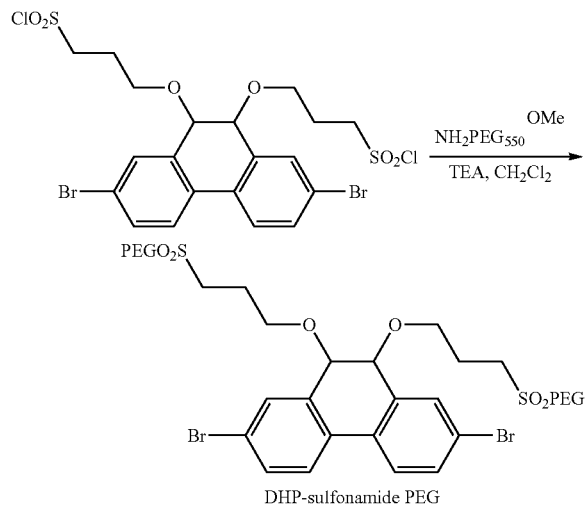

DHP-sulfonamide PEG can be prepared as follows. DHP—OSO$_2$Cl is mixed with 2.2 equivalents of PEG amine in a dichloromethane/TEA mixture. After 3 h sonication, the crude product is extracted in dichloromethane followed by column chromatography (silica gel, MeOH—CHCl$_3$).

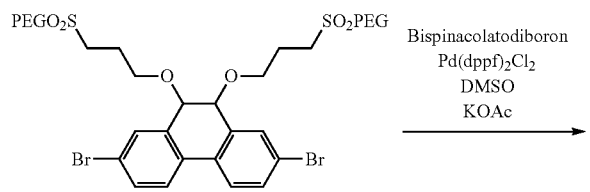

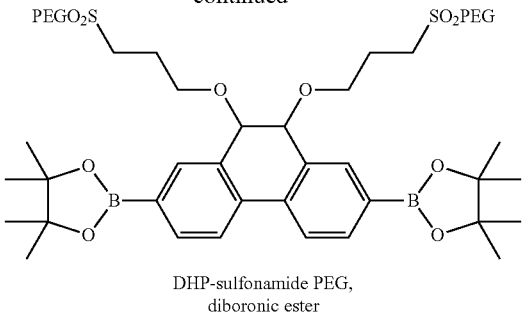

DHP-sulfonamide PEG, diboronic ester

DHP-sulfonamide PEG, diboronic ester, can be prepared as follows. The dibromo-functionalized DHP-sulfonamide is mixed with DMSO under nitrogen and to this 3 equivalent of bispinacolatodiboron is added. The reagents are reacted with 12 equivalents of potassium acetate and 4 equivalents of Pd(dppf)Cl$_2$ catalyst for 5 hours at 80° C. The reaction mixture is cooled and extracted with CHCl$_3$/water. The organic layer is concentrated and purified by column chromatography (silica gel, MeOH—CHCl$_3$).

Similarly, fluorene (FL) monomers of the present invention can be made as described below. For example, FL-OSO$_3$H can be prepared as follows. In a 2 neck round bottom flask, 5 g of fluorene is dissolved in 70 mL of DMSO. The solution is purged with nitrogen (20 min) and 50% NaOH (12 eq) is added while nitrogen purging continues. The color of the solution changes from colorless to dark brown. Propane sultone (3 eq) is weighed and dissolved in DMSO. This is added to the fluorene reaction mixture dropwise over a period of 5 minutes. The reaction is stirred at RT for 4-5 hrs. The solvents are evaporated, and the precipitate is dissolved in water. Acetone is added to obtain a white precipitate of DPS in the form of disodium salt. The precipitate is filtered and redissolved in a small amount of water, neutralized with HCl, and precipitated again in acetone. Repeated precipitation (2-3 times) followed by centrifugation affords FL-OSO$_3$H as white solid.

FL-OSO$_2$Cl can be prepared as follows. 5 g of FL-OSO$_3$H is taken in a round bottom flask and mixed with 25 mL of DMF. To this about 10 mL of SOCl$_2$ is added dropwise and the mixture is allowed to stir overnight. The reaction mixture is then poured into 200 mL water and the precipitate is filtered and dried.

FL-sulfonamide PEG can be prepared as follows. FL-OSO$_2$Cl is mixed with 2.2 equivalents of PEG amine in dichloromethane/TEA mixture. After 3 h of sonication, the crude product is extracted in dichloromethane followed by column chromatography (silica gel, MeOH—CHCl$_3$).

The diboronic ester of FL-sulfonamide PEG can be prepared as follows. The corresponding dibromo-substituted compound is mixed with DMSO under nitrogen and to this 3 equivalent of bispinacolatodiboron is added. The reagents are reacted with 12 equivalents of potassium acetate and 4 equivalents of Pd(dppf)Cl$_2$ for 5 hours at 80° C. The reaction mixture is cooled and extracted with CHCl$_3$/water. The organic layers are concentrated and purified by column chromatography (silica gel, MeOH—CHCl$_3$).

B. Polymerization

Generally, polymerization monomer units described above can be accomplished using polymerization techniques known to those of skill in the art or using methods known in the art in combination with methods described herein. For example, Synthesis of diboronic ester derivatives from a dihalide monomer can be accomplished via Suzuki coupling with bis(pinacolato) diboron:

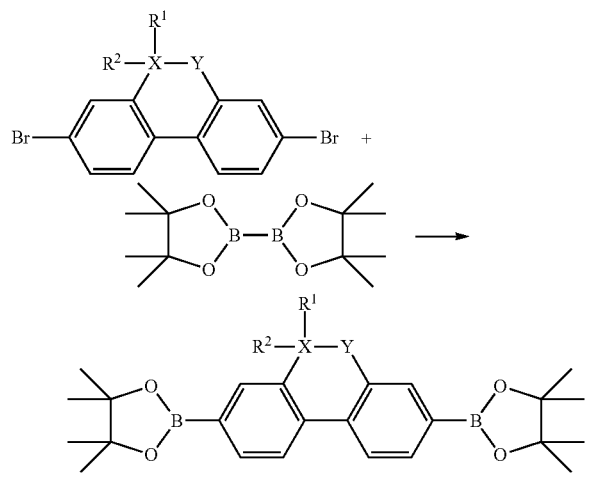

Similarly, polymerization can also be achieved via Suzuki coupling:

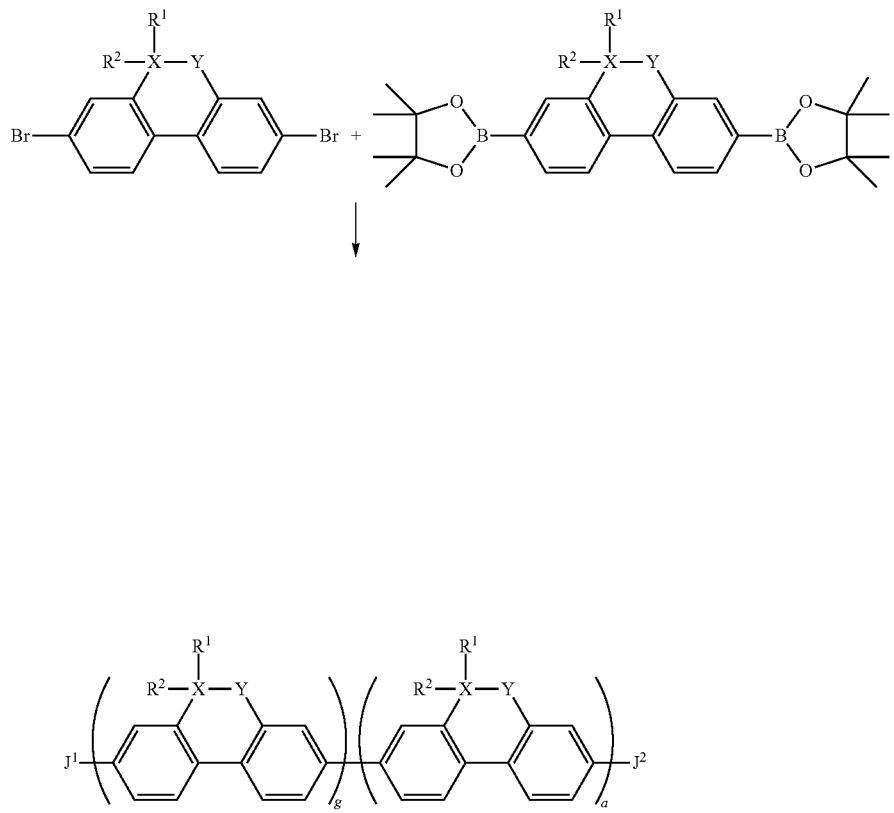

where $J^1$ and $J^2$ are independently H, Br, $B(OH)_2$, or a boronic ester.

For example, polymerization can proceed as follows. In a round bottom flask both the bromo and boronic monomers are dissolved in a DMF-water mixture and purged with nitrogen for 10 minutes. Under nitrogen, about 20 equivalents of CsF and of $Pd(OAc)_2$ (10 mol %) are mixed and heated at 80° C. Polymerization is monitored using UV-Vis spectroscopy and SEC chromatography. Following polymerization, a first capping agent containing appropriate functional groups is added and 3 hours later a second capping agent is added. After the reaction, solvents are removed from the crude mixture via evaporation and the crude material is passed through a gel filtration column to remove small organic molecules and low-MW oligomers.

C. Capping Units

Capping units can be conjugated to a polymer backbone of this invention via similar mechanisms as described previously. For example, bromo- and boronic esters of capping units can be appended to one or both ends of a polymer. Utilizing both bromo groups and boronic esters of capping units will modify both ends of the polymer. Utilizing only one form of a capping unit, either a bromo group or a boronic ester, will modify only those ends terminated with its respective complement and for symmetric polymerizations can be used to statistically modify only one end of a polymer. For asymmetric polymers this approach is used to chemically ensure the polymers are only modified at a single chain terminus. Capping units can also be appended asymmetrically by first reacting a bromo-capping unit with a polymer with Y ends and subsequently reacting the polymer with a boronic ester capping unit.

For example, capping agents of the present invention can be made as shown below.

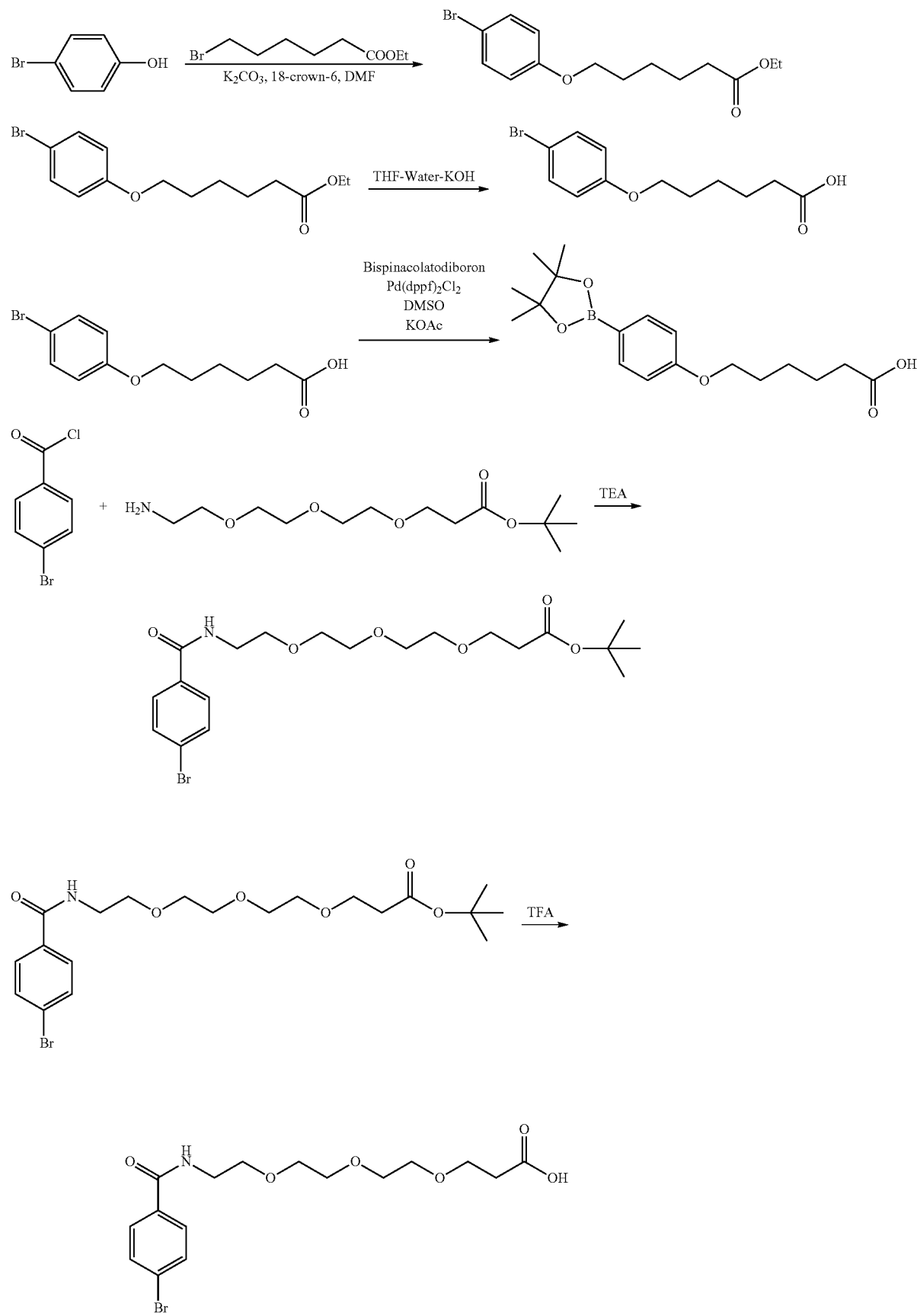

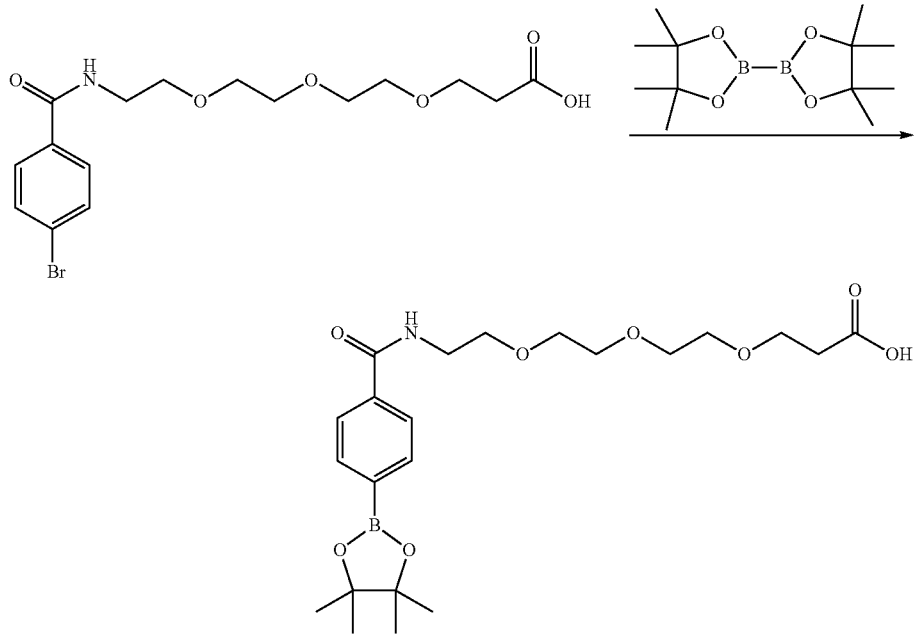

D. Polymer Functionalization

Tandem polymer dyes and other functionalized polymers can be prepared by modification of polymer intermediates after polymerization, as described herein. For example, a pendant solubilizing groups according to Formula IV:

(IV)

can be converted to functionalized solubilizing groups according to Formula V:

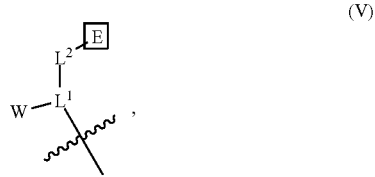
(V)

wherein W is a water solubilizing moiety and $L^1$ and $L^2$ are linking moieties. In some embodiments, each E is an independently selected chromophore, functional moiety, or binding agent. In some embodiments, each E is an independently selected chromophore (e.g., and independently selected fluorophore). In some embodiments, all of the E moieties in the polymer have the same fluorophore structure.

Water solubilizing moieties W in groups according to Formula IV and formula V may be, for example, an ammonium alkyl salt, an ammonium alkyloxy salt, an ammonium oligoether salt, a sulfonate alkyl salt, a sulfonate alkoxy salt, a sulfonate oligoether salt, a sulfonamido oligoether, an oligo(ethylene glycol), or a poly(ethylene glycol). Linking moieties $L^1$, $L^2$, and $L^3$ may be, but are not limited to, a covalent bond, $C_{1-8}$ alkylene, 2- to 8-membered heteroalkylene. In some embodiments, the linker is a single atom, a linear chain, a branched chain, a cyclic moiety. In some embodiments, the linker is chain of between 2 and 100 backbone atoms (e.g., carbon atoms) in length, such as between 2 and 50 backbone atoms in length or between 2 and 20 atoms backbone atoms in length. In certain cases, one, two, three, four or five or more carbon atoms of a linker backbone can be optionally replaced with sulfur, nitrogen, or oxygen. The bonds between backbone atoms can be saturated or unsaturated; typically, not more than one, two, or three unsaturated bonds will be present in a linker backbone. The linker can include one or more substituent groups (e.g., an alkyl group or an aryl group). A linker can include, without limitation, oligo(ethylene glycol); ethers; thioethers; tertiary amines; and alkylene groups (i.e., divalent alkyl radicals), which can be straight or branched. The linker backbone can include a cyclic group, for example, a divalent aryl radical, a divalent heterocyclic radical, or a divalent cycloalkyl radical, where 2 or more atoms, e.g., 2, 3 or 4 atoms, of the cyclic group are included in the backbone.

In some embodiments, $L^1$ comprises a sulfonamide, a sulfinamide, a disulfonamide, a disulfinamide, a sultam, an amide, a secondary amine, a phosphonamide, a phosphinamide, a phosphonamidate, a selenonamide, or a seleninamide. In some embodiments, $L^1$ comprises a sulfonamide, an amide, secondary amine, or a phosphonamide. In some such embodiments, $L^2$ comprises a linear or branched, saturated or unsaturated $C_{1-30}$ alkylene group; wherein one or more carbon atoms in the $C_{1-30}$ alkylene group is optionally and independently replaced by O, S, $NR^a$; wherein two or more groupings of adjacent carbon atoms in the $C_{1-30}$ alkylene are optionally and independently replaced by —$NR^a$(CO)— or —(CO)$NR^a$—; and wherein each $R^a$ is independently selected from H and $C_{1-6}$ alkyl.

In some embodiments, polymers may be functionalized by covalently bonding an internal position of $L^1$ in a pendant solubilizing group according to Formula IV to a first end of linker moiety $L^2$ in a first step, and then covalently bonding a dye, or other functional group E, to a second end of linker moiety $L^2$ in a second step. In some embodiments, a nitrogen atom in $L^1$ (e.g., an amide nitrogen, a sulfonamide nitrogen, or a phosphonamide nitrogen) is alkylated using a linker moiety $L^2$ having a suitable leaving group at the first end of the linker moiety. In some embodiments, for example, the leaving group is a halogen (e.g., chloro, bromo, or iodo). In some embodiments the leaving group is a sulfonate (i.e., —OS(O)$_2$R, wherein R is alkyl, haloalkyl, aryl, or substituted aryl). Suitable sulfonates include, but are not limited to, mesylate (methanesulfonate), triflate (trifluoromethanesulfonate), besylate (benzene-sulfonate), tosylate (p-toluenesulfonate), and brosylate (4-bromobenzenesulfonate).

Any suitable solvent can be used for alkylation steps during polymer functionalization. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. Alkylation reactions are typically conducted at temperatures ranging from around 25° C. to about 100° C. for a period of time sufficient install a linking moiety $L^2$, or a linked functional group —$L^2$—E, at one or more pendant groups in the polymer. The reaction can be conducted for a period of time ranging from a few minutes to several hours or longer, depending on the polymer and reagents used in the reaction. For example, the reaction can be conducted for around 10 minutes, or around 30 minutes, or around 1 hour, or around 2 hours, or around 4 hours, or around 8 hours, or around 12 hours at around 40° C., or around 50° C., or around 60° C., or around 70° C., or around 80° C.

The second end of the linking moiety $L^2$ may comprise a functional group (e.g., an amine or a carboxylic acid) which is used in protected form during the first step (e.g., an alkylation step) and which is then deprotected prior to covalently bonding the dye, or other functional group E, to the second end of linking moiety. Examples of amine protecting groups include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. These and other protecting groups for amines, carboxylic acids, alcohols, and further functional groups can be added to and removed from polymers of the present disclosure using known techniques as described, for example, by Green and Wuts (*Protective Groups in Organic Synthesis*, 4$^{th}$ Ed 2007, Wiley-Interscience, New York).

Addition of dyes and other functional groups can be conducted using any suitable method. In some embodiments, an amide linkage is formed between a deprotected primary amine group of $L^2$ and carboxylate-functionalized dye. The dye may be used in activated form, e.g., as a reagent E-C(O)X can be used, wherein X is a leaving group. Activated carboxylate-functionalized reagents include, but are not limited to, anhydrides (including symmetric, mixed, or cyclic anhydrides), activated esters (e.g., p-nitrophenyl esters, pentafluorophenyl esters, N-succinimidyl esters, and the like), acylazoles (e.g., acylimidazoles, prepared using carbonyl diimidazole, and the like), acyl azides, and acid halides (e.g., acid chlorides). Alternatively, a coupling agent may be used to form a bond the amide linkage between a deprotected primary amine group of $L^2$ and carboxylate-functionalized chromophore E—C(O)OH. The coupling agent may be used to form activated dye reagents prior to reaction with polymer amine groups. Any suitable coupling agent may be used. In some embodiments, the coupling agent is a carbodiimide, a guanidinium salt, a phosphonium salt, or a uronium salt. Examples of carbodiimides include, but are not limited to, N,N'-dicyclohexylcarbodiimide (DCC), 1-ethyl-3-(3-dimethylaminopropyl)-carbodiimide (EDC), and the like. Examples of phosphonium salts include, but are not limited to, such as (benzotriazol-1-yloxy)tripyrrolidinophosphonium hexafluorophosphate (PyBOP); bromotris(dimethylamino)phosphonium hexafluorophosphate (BroP); and the like. Examples of guanidinium/uronium salts include, but are not limited to, N,N,N',N'-tetramethyl-O—(N-succinimidyl)uronium tetrafluoroborate (TSTU); O-(benzotriazol-1-yl)-N,N,N',N'-tetramethyl-uronium hexafluorophosphate (HBTU); 2-(7-aza-1H-benzotriazole-1-yl)-1,1,3,3-tetramethyl-uronium hexafluorophosphate (HATU); 1-[(1-(cyano-2-ethoxy-2-oxoethylideneaminooxy) dimethylaminomorpholino)]uronium hexafluorophosphate (COMU); and the like. Solvents, reaction times, and other reaction conditions can be varied as described above depending on factors such as the nature of the particular polymer and dye/functional group.

Some embodiments of the present disclosure provide a method of making a conjugated polymer according to Formula II:

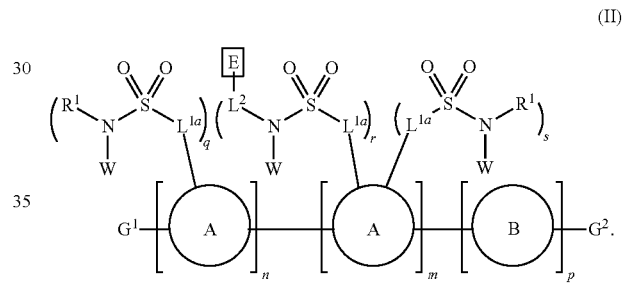

(II)

The method includes converting a conjugated polymer according to Formula IIa:

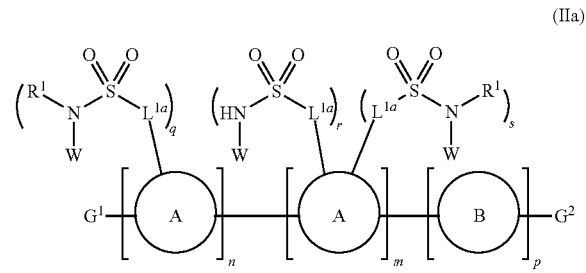

(IIa)

to the polymer according to Formula II, wherein:

A is a fluorescent monomer;

$L^{1a}$ is selected from the group consisting of a covalent bond, $C_{1-8}$ alkylene, 2- to 8-membered heteroalkylene, —NHC(O)$L^a$—, —C(O)NHL$^a$—, and —C(O)$L^a$—;

$L^2$ is selected from the group consisting of a covalent bond, $C_{1-8}$ alkylene, 2- to 8-membered heteroalkylene, —$L^b$NHC(O)—, —$L^b$C(O)NH—, —$L^b$C(O)—, —C(O)NHL$^b$—, and —C(O)$L^b$—;

$L^a$ and $L^b$ are independently selected from the group consisting of $C_{1-8}$ alkylene and 2- to 8-membered heteroalkylene;

W is a water-solubilizing moiety;

each E is an independently selected chromophore, functional moiety, or binding agent;

each B is independently selected from the group consisting of an aromatic co-monomer, a heteroaromatic co-monomer, a bandgap-modifying monomer, optionally substituted ethylene, and optionally substituted ethynylene;

$G^1$ and $G^2$ are independently selected from an unmodified polymer terminus and a modified polymer terminus;

$R^1$ is selected from the group consisting of H and an amine protecting group;

subscripts n and m are independently integers ranging from 1 to 10,000, subscript p is an integer ranging from 0 to 10,000, and the sum of subscripts n, m, and p ranges from 2 to 10,000;

subscript q is 1, 2, 3, or 4;

subscript r is 1, 2, 3, or 4;

subscript s is 0, 1, 2, or 3;

subscript t is 1 or 2

A and B are distributed randomly or non-randomly in the fluorescent polymer.

In some embodiments, converting the conjugated polymer of Formula IIa to the conjugate polymer according to Formula II includes one or more alkylation steps, or one or more amide formation steps, as described above.

Any suitable chromophore or fluorophore can be used for polymer functionalization. In general, suitable chromophores and fluorophores have a reactive group (e.g., a carboxylate moiety, an amino moiety, a haloalkyl moiety, or the like) that can be covalently bonded to the pendant solubilizing groups (e.g., via linking moieties $L^2$ as described above). Examples of suitable chromophores and fluorophores include, but are not limited to, those described in U.S. Pat. Nos. 7,687,282; 7,671,214; 7,446,202; 6,972,326; 6,716,979; 6,579,718; 6,562,632; 6,399,392; 6,316,267; 6,162,931; 6,130,101; 6,005,113; 6,004,536; 5,863,753; 5,846,737; 5,798,276; 5,723,218; 5,696,157; 5,658,751; 5,656,449; 5,582,977; 5,576,424; 5,573,909; and 5,187,288, which patents are incorporated herein by reference in their entirety.

In some embodiments, the chromophore E is a borondipyrromethene moiety having the structure:

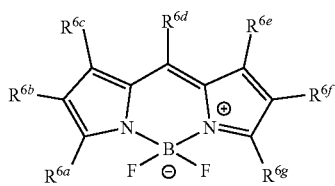

wherein six of $R^{6a}$, $R^{6b}$, $R^{6c}$, $R^{6d}$, $R^{6e}$, $R^{6f}$, and $R^{6g}$ are independently selected from H, halogen, $C_{1-6}$ alkyl, $C_{3-8}$ cycloalkyl, $C_{6-10}$ aryl, $C_{7-16}$ arylalkyl, $C_{1-6}$ acyl, and —$SO_3H$; and wherein one of $R^{6a}$, $R^{6b}$, $R^{6c}$, $R^{6d}$, $R^{6e}$, $R^{6f}$, and $R^{6g}$ is the linking moiety -$L^2$-.

In some embodiments, $R^{6a}$ and $R^{6c}$ are independently selected $C_{1-6}$ alkyl (e.g., methyl or ethyl), and one of $R^{6e}$, $R^{6f}$, and $R^{6g}$ is the linking moiety —$L^2$—. In some embodiments, $R^{6a}$ and $R^{6c}$ are methyl and $R^{6g}$ is the linking moiety —$L^2$—.

In some embodiments, the chromophore E is a cyanine moiety having the structure:

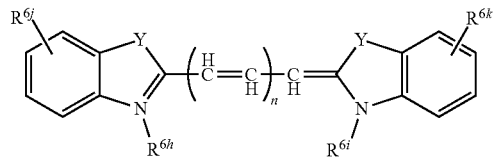

wherein $R^{6h}$ and $R^{6i}$ are independently selected from H, $C_{1-6}$ alkyl, $(CH_2)_tCOOH$, $(CH_2)_tSO_3H$, and linking moiety $L^2$;

each subscript t is independently an integer from 1 to 10;

$R^{6j}$ and $R^{6k}$ are independently selected from H, halogen, $C_{1-6}$ alkyl, optionally substituted fused $C_{6-10}$ aryl (e.g., optionally substituted benzo), —$SO_3H$, —$PO_3H_2$, —$OPO_3H_2$, —COOH, and linking moiety $L^2$;

each Y is independently selected from O, S, $C(R^{6l})_2$, —CH=CH—, and $NR^{6l}$, where each $R^{6l}$ is independently H or $C_{1-6}$ alkyl; and subscript n is an integer from 1 to 6, provided that one and only one of $R^{6h}$, $R^{6i}$, $R^{6j}$, and $R^{6k}$ is the linking moiety —$L^2$—.

In some embodiments, the chromophore E is a coumarin moiety having the structure:

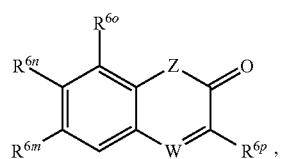

wherein

W is N or $CR^{6p}$;

Z is O, S, or $NR^{6q}$; and each of $R^{6m}$, $R^{6n}$, $R^{6o}$, $R^{6p}$ is independently selected from H, halogen, $C_{1-6}$ alkyl, —CN, —$CF_3$, —$COOR^{3v}$, —$CON(R^{3v})_2$, —$OR^{3v}$, and linking moiety —$L^2$—;

$R^{6n}$ is selected from —$OR^{3v}$ and —$N(R^{3v})_2$ each $R^{6q}$ is independently selected from H, $C_{1-6}$ alkyl, and linking moiety —$L^2$—;

provided that one and only one of $R^{6m}$, $R^{6n}$, $R^{6o}$, $R^{6p}$ and $R^{6q}$ is the linking moiety —$L^2$—.

In some embodiments, chromophore E is a xanthene moiety having the structure:

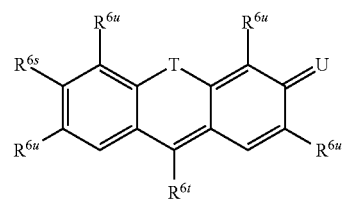

wherein:

T is selected from O, S, $C(R^{6u})_2$, and $NR^{6u}$:

U is O or $N(R^{6u})_2$;

each $R^{6r}$ is independently selected from H, halogen, $C_{1-6}$ alkyl, —$SO_3H$, and linking moiety —$L^2$—;

$R^{6s}$ is selected from H, —OH, —OR$^{6u}$, —N(R$^{6u}$)$_2$, and linking moiety —L$^2$—;

$R^{6t}$ is selected from H, C$_{1-6}$ alkyl, R$^{6v}$, and linking moiety —L$^2$—;

each R$^{6u}$ is independently H or C$_{1-6}$ alkyl; and

R$^{6v}$ is selected from

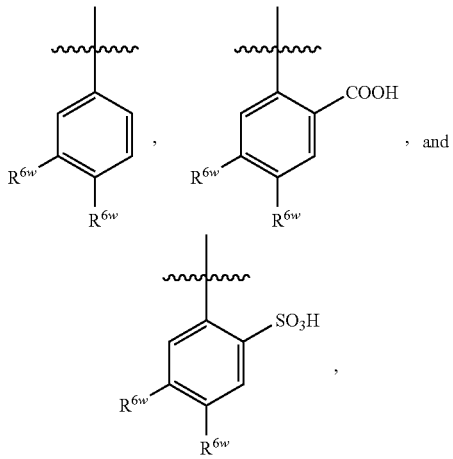

wherein:

each R$^{6w}$ is independently selected from H and linking moiety —L$^2$—;

provided that one and only one of R$^{6r}$, R$^{6s}$, R$^{6t}$, and R$^{6v}$ is linking moiety —L$^2$—.

In some embodiments, the xanthene moiety is a fluorescein, wherein T and U are O; R$^{6s}$ is OH, and R$^{6t}$ is:

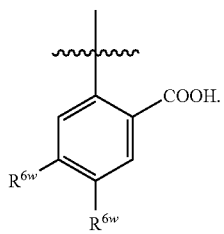

In some embodiments, the xanthene moiety is an eosin, wherein T and U are O; R$^{6s}$ is OH, each R$^{6r}$ is halogen (e.g., bromo), and R$^{6t}$ is:

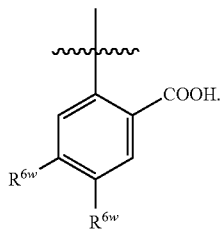

In some embodiments, the xanthene moiety is a rhodamine, wherein T is O; U is N(R$^{6u}$)$_2$ (e.g., =NH$_2^+$); R is —N(R$^{6u}$)$_2$ (e.g., —NH$_2$), and R$^{6t}$ is:

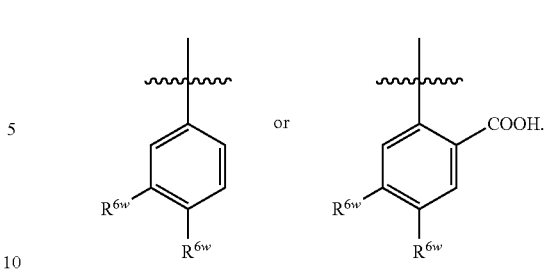

In some embodiments, the xanthene moiety is a rhodamine having the structure:

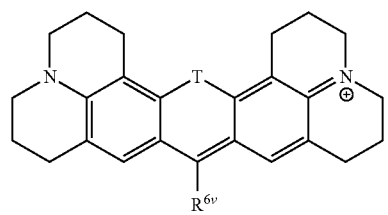

wherein R$^{6v}$ is selected from

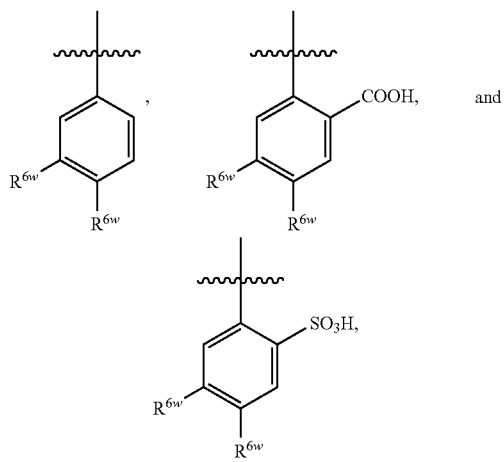

one R$^{6w}$ is H, and the other R$^{6w}$ is linking moiety —L$^2$—.

Other functional moieties, in addition to chromophores, can be appended to functionalized polymers using the methods provided herein. For example, a functional moiety "E" can be a biotin, a digoxigenin, a peptide tag such as a FLAG peptide, an oligonucleotide, or a polynucleotide. As used herein, the term "FLAG peptide" refers to an oligopeptide or a polypeptide containing the amino acid sequence Asp-Tyr-Lys-Asp-Asp-Asp-Asp-Lys (i. e., DYKDDDDK). FLAG peptides and variants thereof are described for example, in U.S. Pat. No. 4,703,004 to Hopp, et al., which patent is incorporated herein by reference. Other peptides that can be used in place of a FLAG peptide include, but are not limited to, HA peptide tags containing the sequence Tyr-Pro-Tyr-Asp-Val-Pro-Asp-Tyr-Ala (i.e., YPYDVPDYA), His$_6$ peptide tags containing the sequence His-His-His-His-His-His (i.e., HHHHHH), and Myc peptide tags containing the sequence Glu-Gln-Lys-Leu-Ile-Ser-Glu-Glu-Asp-Leu (i.e., EQKLISEEDL). The peptide tags can be recognized by antibodies or other binding moieties for use with colorimetric reagents, chemiluminescent reagents, or the like for convenient identification and/or quantification. Nucleotides (e.g., RNA, single-stranded DNA, or double-stranded DNA) can be recognized by a complementary primer or other complementary nucleotide as described, for example, in WO 2016/019929 (Navratil, et al.), which publication is incorporated herein by reference. As used herein, the term "digoxigenin" refers to 3-[(3S,5R,8R,9S,10S,12R,13S,14S,17R)-3,12,14-trihydroxy-10,13-dimethyl-1,2,3,4,5,6,7, 8,9,11,12,15,16,17-tetradecahydrocyclopenta[a]-phenanthren-17-yl]-2H-furan-5-one (CAS Registry No. 1672-46-4) and substituted analogs thereof. As used herein, the term "biotin" refers to 5-[(3aS,4S,6aR)-2-oxohexahydro-1H-thieno[3,4-d]imidazol-4-yl]pentanoic acid (CAS Registry No. 58-85-5) and substituted analogs thereof.

E. Binding Agents

A "binding agent" of the invention can be any molecule or complex of molecules capable of specifically binding to target analyte. A binding agent of the invention includes for example, a protein (e.g., an antibody or an antibody fragment), a small organic molecule, a carbohydrate (e.g., a polysaccharide), an oligonucleotide, a polynucleotide, a lipid, an affinity ligand, an aptamer, or the like. In some embodiments, the binding agent is an antibody or fragment thereof. Specific binding in the context of the present invention refers to a binding reaction which is determinative of the presence of a target analyte in the presence of a heterogeneous population. Thus, tinder certain assay conditions, the specified binding agents bind preferentially to a particular protein or isoform of the particular protein and do not bind in a significant amount to other proteins or other isoforms present in the sample.

When the binding agents are antibodies, they may be monoclonal or polyclonal antibodies. The term antibody as used herein refers to immunoglobulin molecules and immunologically active portions of immunoglobulin (Ig) molecules. Such antibodies include, but are not limited to, polyclonal, monoclonal, mono-specific polyclonal antibodies, antibody mimics, chimeric, single chain, Fab, Fab' and F(ab')$_2$ fragments, Fv, and an Fab expression library.

In some cases, the antibody includes intravenous immunoglobulin (IVIG) and/or antibodies from (e.g., enriched from, purified from, e.g., affinity purified from) IVIG. IVIG is a blood product that contains IgG (immunoglobulin G) pooled from the plasma (e.g., in some cases without any other proteins) from many (e.g., sometimes over 1,000 to 60,000) normal and healthy blood donors. IVIG is commercially available. Aspects of IVIG are described, for example, in US. Pat. Appl. Pub. Nos. 2010/0150942; 2004/0101909; 2013/0177574; 2013/0108619; and 2013/0011388.

In some cases, the antibody is a monoclonal antibody of a defined sub-class (e.g., IgG1, IgG2, IgG3, or IgG4). If combinations of antibodies are used, the antibodies can be from the same subclass or from different subclasses. For example, the antibodies can be IgG1 antibodies. In some embodiments, the monoclonal antibody is humanized.

In some embodiments, the antibody is capable of binding one or more targets selected from BRCA1, CTLA4, CD4, EGF, EGFR, ERBB2 (Her-2), IFN-a, IFNgamma, IL-1, IL1R1 (CD121a), IL1R2(CD121b), IL-IRA, IL-2, IL2RA (CD25), IL2RB(CD122), IL2RG(CD132), IL-4, IL-4R (CD123), IL-5, IL5RA(CD125), IL3RB(CD131), IL-6, IL6RA, (CD126), IR6RB(CD130), IL-7, IL7RA(CD127), IL-8, CXCR1 (IL8RA), CXCR2, (IL8RB/CD128), IL-9, IL9R(CD129), IL-10, IL10RA(CD210), IL10RB (CDW210B), IL-11, IL11 RA, IL-12, IL-12A, IL-12B, IL-12RB1, IL-12RB2, IL-13, IL13RA1, IL13RA2, IL14, IL15, IL15RA, IL16, IL17, IL17A, IL17B, IL17C, IL17R, JAG1, JAK1, JAK3, mTOR, MUC1 (mucin), MYC, NOTCH, NOTCH1, NOX5, PI3 Kinase, PIK3CG, PTEN, PTN, TLR10, TLR2, TLR3, TLR4, TLR5, TLR6, TLR7, TLR8, TLR9, TNF, TNF-a, TNFSF5 (CD40 ligand), TNFSF6 (FasL), TNFSF7 (CD27 ligand), TNFSF8 (CD30 ligand), TNFSF9 (4-1BB ligand), TOLLIP, TOP2A (topoisomerase Iia), VEGFB, VEGFB, VEGFC, versican, VHL C5, VLA-4, Wnt-1. Examples of antibodies for polymer conjugation include, but are not limited to, adalimumab (also known as HUMIRA™), adecatumumab, alemtuzumab, bertilimumab, brentuximab, cetuximab (also known as ERBITUX™), clenoliximab, dacetuzumab, dacliximab, daclizumab (also known as ZENAPAX™), detumomab, dorlixizumab, duntumumab, gemtuzumab, infliximab (also known as REMICADE™), ipilimumab (also known YERVOY™), lumiliximab, mapatumumab maslimomab, nebacumab, nerelimomab, pembrolizumab (also known as KEYTRUDA™) regavirumab, reslizumab, rituximab (also known as RITUXAN™, MabTHERA™), rovelizumab, tadocizumab, and trastuzumab (also known as HERCEPTIN™).

In general, polymers of the present invention can be conjugated to binding agents using techniques known to those of skill in the art or using methods known in the art in combination with methods described herein. Binding agents can also be installed at the "E" position in polymers according to Formula I via linker moieties $L^1$, $L^2$, and $L^3$ as described above.

For example, preparation of a polymer NHS ester can proceed as follows. 5 mg of the polymer is dissolved in 1 mL of dry $CH_3CN$. To this is added 15 mg TSTU, and the mixture is stirred for 2 more minutes. To this is add 100 µL of DIPEA and stirring is continued overnight. Next, the organic solvents are removed via evaporation, and the crude NHS product is dissolved in about 750 µL of 1×PBS buffer (pH 8.8) by a quick vortex before transfer to a Zeba spin column (40K MWCO). The sample at is spun at 2200 RPM for 2 min and the polymer NHS ester is used immediately.

Conjugation of the polymer NHS ester with an antibody (e.g., a CD4 mAb) can proceed as follows. The polymer NHS ester in PBS buffer is added to 0.6 mg of the antibody and mixed with 100 µL. of 0.5M Borate buffer (pH 9.0). The mixture is vortexed quickly for 30 seconds and then allowed to mix for 3-4 hours in a Coulter mixer.

Purification of His-tagged antibody conjugates through a Histrap HP column can proceed as follows. Approach 1: The crude reaction mixture is purified using a Histrap HP column. The sample is loaded using 1×PBS buffer and the unbound fraction is collected. This can be done using 20 column volumes of buffer, Later, the buffer is changed to wash the bound fraction which has both conjugate and free antibody. This can be done using 1×PBS with 0.25 M imidazole running for 10 column volumes.

Approach 2: Hitrap SP Sepharose FF column. The column is equilibrated, the crude reaction mixture is loaded using 20 mM citrate buffer, pH 3.5, and the unbound fraction is collected. This can be done using 20 column volumes of buffer. Later, the buffer is changed to elute the bound fraction which has both conjugate and free antibody. This can be done using 20 mM citrate, pH 7.6, containing 0.6 M NaCl, running for 20 column volumes.

Purification of conjugate through SEC column can proceed as follows. The reaction mixture is loaded on a size exclusion column using 1×PBS. Fractions are pooled after checking UV-visible absorption spectra and concentrated in a Amicon Ultra-15 tube having a 30 kDa MWCO centrifugal concentrator.

Polymers bearing Michael acceptors such a maleimides can be covalent bonded to thiols present in cysteine residues of antibodies as described in more detail below. Free thiols can be generated by reduction of interchain disulfide bonds, or free thiols can be introduced as engineered (i.e., non-naturally occurring) cysteine residues. Engineered cysteine residues can be located in the antibody heavy chains or the antibody light chains. In certain embodiments, engineered cysteine residues are located in the Fc region of the heavy chains. Engineered antibodies as described, for example, in U.S. Pat. Nos. 7,855,275; 8,309,300; and 9,000,130, can be employed.

IV. Methods of Detecting an Analyte

A. Overview

Also provided are methods for detecting an analyte in a sample comprising: providing a sample that is suspected of containing an analyte; and combining the sample with a conjugated polymer complex comprising a binding agent conjugated to a water soluble conjugated polymer as described herein. The binding agent is capable of interacting with the analyte. A light source is applied to the sample that can excite the polymer and light emitted from the conjugated polymer complex is detected. In the typical assay, fluorescent polymers of the invention are excitable with a light having wavelength between about 395 nm and about 415 nm. The emitted light is typically between about 415 nm and about 475 nm. Alternatively, excitation light can have a wavelength between about 340 nm and about 370 nm and the emitted light is between about 390 nm and about 420 nm.

B. Sample

The sample in the methods of the present invention can be, for example, blood, bone marrow, spleen cells, lymph cells, bone marrow aspirates (or any cells obtained from bone marrow), urine (lavage), serum, saliva, cerebral spinal fluid, urine, amniotic fluid, interstitial fluid, feces, mucus, or tissue (e.g., tumor samples, disaggregated tissue, disaggregated solid tumor). In certain embodiments, the sample is a blood sample. In some embodiments, the blood sample is whole blood. The whole blood can be obtained from the subject using standard clinical procedures. In some embodiments, the sample is a subset of one or more cells of whole blood (e.g., erythrocyte, leukocyte, lymphocyte (e.g., T cells, B cells or NK cells), phagocyte, monocyte, macrophage, granulocyte, basophil, neutrophil, eosinophil, platelet, or any cell with one or more detectable markers). In some embodiments, the sample can be from a cell culture.

The subject can be a human (e.g., a patient suffering from a disease), a commercially significant mammal, including, for example, a monkey, cow, or horse. Samples can also be obtained from household pets, including, for example, a dog or cat. In some embodiments, the subject is a laboratory animal used as an animal model of disease or for drug screening, for example, a mouse, a rat, a rabbit, or guinea pig.

C. Analytes

An "analyte" as used herein, refers to a substance, e.g., molecule, whose abundance/concentration is determined by some analytical procedure. For example, in the present invention, an analyte can be a protein, peptide, nucleic acid, lipid, carbohydrate or small molecule.

The target analyte may be, for example, nucleic acids (DNA, RNA, mRNA, tRNA, or rRNA), peptides, polypeptides, proteins, lipids, ions, monosaccharides, oligosaccharides, polysaccharides, lipoproteins, glycoproteins, glycolipids, or fragments thereof. In some embodiments, the target analyte is a protein and can be, for example, a structural microfilament, microtubule, and intermediate filament proteins, organelle-specific markers, proteasomes, transmembrane proteins, surface receptors, nuclear pore proteins, protein/peptide translocases, protein folding chaperones, signaling scaffolds, ion channels and the like. The protein can be an activatable protein or a protein differentially expressed or activated in diseased or aberrant cells, including but not limited to transcription factors, DNA and/or RNA-binding and modifying proteins, nuclear import and export receptors, regulators of apoptosis or survival and the like.

D. Assays

Assay systems utilizing a binding agent and a fluorescent label to quantify bound molecules are well known. Examples of such systems include flow cytometers, scanning cytometers, imaging cytometers, fluorescence microscopes, and confocal fluorescent microscopes.

In some embodiments, flow cytometry is used to detect fluorescence. A number of devices suitable for this use are available and known to those skilled in the art. Examples include BCI Navios, Gallios, Aquios, and CytoFLEX flow cytometers.

In other embodiments, the assay is an immunoassay. Examples of immunoassays useful in the invention include, but are not limited to, fluoroluminescence assay (FLA), and the like. The assays can also be carried out on protein arrays.

When the binding agents are antibodies, antibody or multiple antibody sandwich assays can also be used. A sandwich assay refers to the use of successive recognition events to build up layers of various binding agents and reporting elements to signal the presence of a particular analyte. Examples of sandwich assays are disclosed in U.S. Pat. No. 4,486,530 and in the references noted therein.

V. Examples

Example 1. Preparation of NHBoc Polymer 50 mg of violet excitable base polymer (1) was prepared as described in WO 2017/180998 and weighed in a 4 mL vial. 800 µL of anhydrous DMF was added to the vial, and the mixture was vortexed and sonicated for 5 minutes to dissolve the polymer completely. Polymer (1) contained an average of 48 PEG-functionalized DH-IP monomers (m=~24); polymers ranging in size (e.g., m=~5-50, n=~5-25) can be prepared in similar fashion.

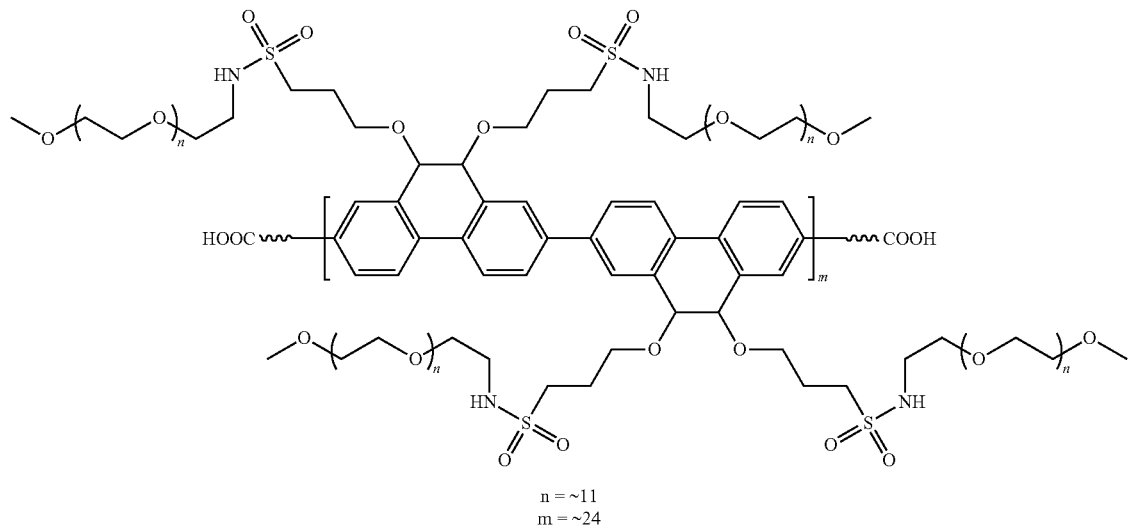

n = ~11
m = ~24

Under nitrogen atmosphere, the polymer solution was transferred to a 10 mL reaction flask containing cesium carbonate (100 eq.). tert-Butyl-3-iodopropyl-carbamate solution was diluted from a stock solution (10 mg/mL in anhydrous DMF), and 10 eq. was added to the polymer mixture. The sealed reaction flask was heated to 50° C., and the reaction was continued for 1 h under stirring at 500 rpm. The reaction mixture was cooled to RT and the DMF was evaporated in a rotary evaporator under high vacuum. The crude reaction mixture was diluted with chloroform (25 mL) and washed with 15% w/v brine solution (25 mL). The organic layer was collected in a 250-mL conical flask, additional chloroform (12 mL) was added, and the mixture was washed three times with 30% w/v brine solution (10 mL). The organic fraction was dried by adding 20 g anhydrous sodium sulfate and then filtered through Whatman Paper 2 into a 150 mL flat bottom flask. The filtered sodium sulfate was washed twice with chloroform (15 mL) to recover the remaining polymer dye and filtered into the same flat bottom flask. The chloroform was evaporated in a rotary evaporator at 45° C. and 150-200 rpm. Residual DMF was removed under a high vacuum pump at 50° C. for 30-40 minutes. The dried polymer was washed with diethyl ether (2×2 mL) and sonicated for two minutes to eliminate the unreacted tert-butyl-3-iodopropyl-carbamate. After drying the polymer under high vacuum for 5 min, the yield of the polymer was calculated with respect to the initial polymer amount. The dried polymer product (2) was characterized using $^1$H NMR; proton signals at 1.4 ppm indicate the existence of NHBoc moieties in polymer. Modified monomers (subscripted m1) and unmodified monomers (subscripted m2) were randomly distributed along the polymer backbone.

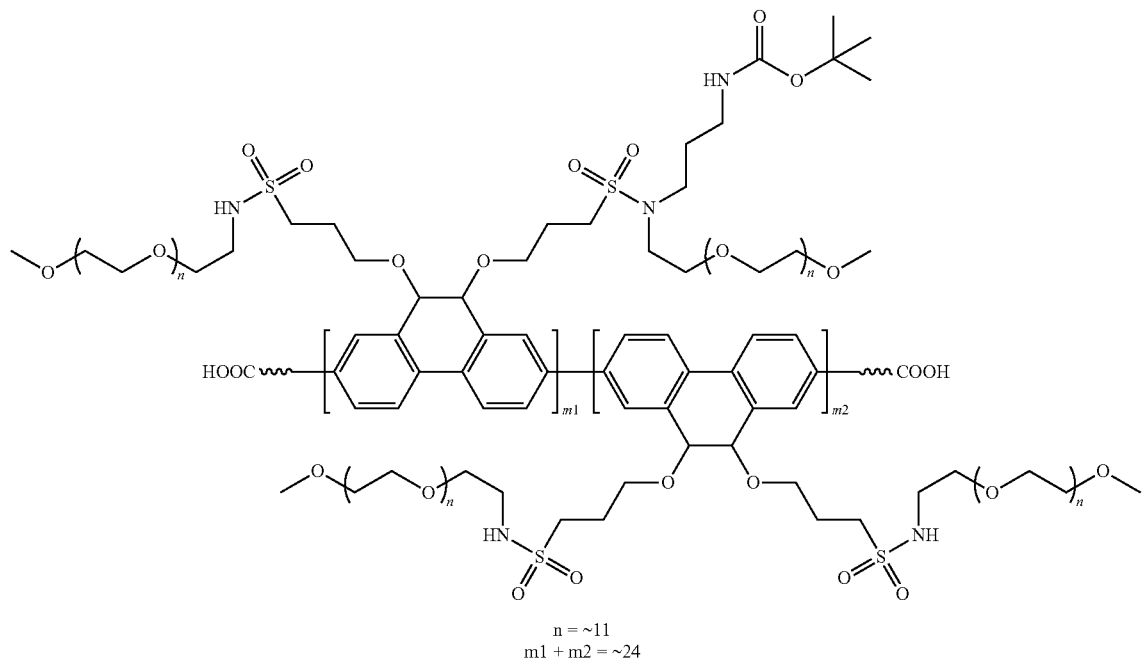

n = ~11
m1 + m2 = ~24

Example 2. Preparation of Amine-Functionalized Polymer 50 mg of the NHBoc polymer prepared according to Example 1 was added to a 20 mL round-bottom flask and dissolved in 1 mL methanol and 1 mL water by vortexing for 5 minutes & sonication for 5 minutes. To the resulting solution was added 12 M HCl (2 mL) and the mixture was allowed to react for 2 h at room temperature. The reaction mixture was then transferred to a small beaker, the pH was adjusted to 9-10 using 150% w/v $K_2CO_3$ solution, and stirred for an additional 15 minutes. The polymer was extracted with 25 mL chloroform in a 100 mL separation funnel, the organic layer was and collected in a conical flask. Brine solution (15% w/v) was added to the aqueous layer and additional portions of chloroform were used to recover remaining polymer. The extraction process was monitored with a UV lamp.

The organic layer was dried using ~40 g anhydrous sodium sulfate and filtered through Whatman filter paper 2 into a 250 mL flat bottom flask. Additional chloroform washes (2×20 mL) were used to recover remaining polymer from the filtered sodium sulfate. The combined chloroform layer was evaporated in a rotary evaporator at about 40° C. After complete solvent evaporation, the solid was dissolved again chloroform (10 mL) and centrifuged at 3000 rpm for 5 min to remove the salt impurities in a 15 mL Falcon tube. The supernatant was decanted in 20 mL vial and concentrated on a rotary evaporator and dried under high vacuum. The yield of the deprotected amine-functionalized polymer (3) was calculated with respect to the protected polymer amount. The deprotection was confirmed by $^1$NMR, and also by determining the acceptor attachment A/D ratio.

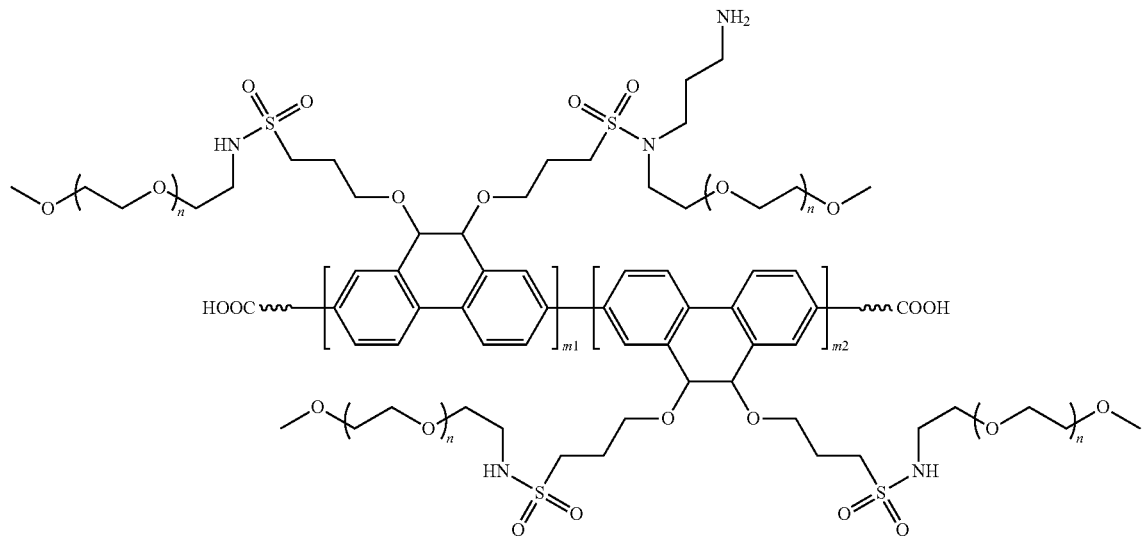

3

Example 3. Tandem Polymer Dye-Antibody Conjugation and Purification

Polymer-Acceptor Dye Formation.

10 mg of polymer was weighed in a glass vial and dissolved in 200 μL of anhydrous DMSO. To ensure the polymer was completely dissolved, a combination of vortex, sonication, and incubation at 50° C. water bath in about 10-15 min were applied. To this, 200 μL acetonitrile and 20 μL diisopropylethylamine were added. A 10 mg/mL (w/v) solution of acceptor dye (near-IR absorbing Dy752NHS; Dyomics GmbH) was prepared in anhydrous DMSO, and 8 equivalents of dye were added to the polymer solution. The mixture was stirred for two hours at room temperature, protected from light, resulting in a product containing an average of 2-3 dyes per polymer chain. Products containing 1-6 dyes per polymer chain can be prepared by adjusting the amount of acceptor dye used in the reaction. Tandem polymer dyes were also prepared with Cy3.5 acceptors using Cy3.5-NHS (Lumiprobe Corp.) as described above for Dy752.

Preparation of Polymer-Acceptor Dye Maleimide.

After 2 hours, TSTU (20 mg) dissolved in 50 μL of acetonitrile was added to the polymer-acceptor dye mixture and the activation process was carried out for 30 min at RT by constant stirring, protect from light.

Two 5 mL 40 K Zeba spin columns were equilibrated with 20 mM borate pH 8.8 buffer, proceeded as described by the manufacturer. At the same time, a 2 mg solution of N-(2-aminoethyl)maleimide trifluoroacetate salt was prepared using 20 μL anhydrous DMSO and kept in the Zeba collection tube.

The activated tandem polymer was dissolved in 1800 μL of 20 mM borate pH 8.8 buffer and combined with the maleimide using the equilibrated Zeba spin column. The polymer amount after the Zeba column step was estimated by measuring the UV 414 of tandem polymer. Approximately 5 mg of tandem polymer was recovered (i.e., around 50 mol %). The resulting mixture of tandem polymer-maleimide was incubated by rolling at RT for 60-120 minutes. Optionally, the reaction can be conducted with sonication for 90 min.

During the incubation period, a 30% ethanol water and a 50 mM MOPS, 100 mM sodium perchlorate, 4 mM EDTA pH 7.0 (MOPS buffer) were prepared. After the reaction, the tandem polymer-maleimide was washed using a 30 or 50 kDa MWCO Amicon concentrator with at least 30-40 mL 30% ethanol water, followed by buffer exchange to MOPS buffer using at least 30-40 mL of MOPS buffer. The final volume of the buffer exchanged polymer-maleimide is between 2-4 mL. This mixture containing maleimide-functionalized tandem dye polymer (4) was stored at 4° C. overnight before further usage.

Preparation of Polymer-Antibody Conjugate.

A 0.5 mL 40 K Zeba column was equilibrated using 1×PBS and 1 mg CD4 mAb was passed through the equilibrated Zeba column. To the buffer exchanged mAb, 30 μL of 10 mg/mL (w/v) (prepared in 1×PBS) DTT (approximately 300 equivalent) was added and the resulting mixture was incubated at RT for 30 min. A 50 mM MES, 0.1 M sodium perchlorate, 4 mM EDTA pH 5.8 (MES buffer) was prepared and kept aside in the dark. After 30 min, the reduced mAb was diluted to 500 μL and passed through a 2 mL 40 K Zeba column pre-equilibrated with MES buffer to remove excess DTT.

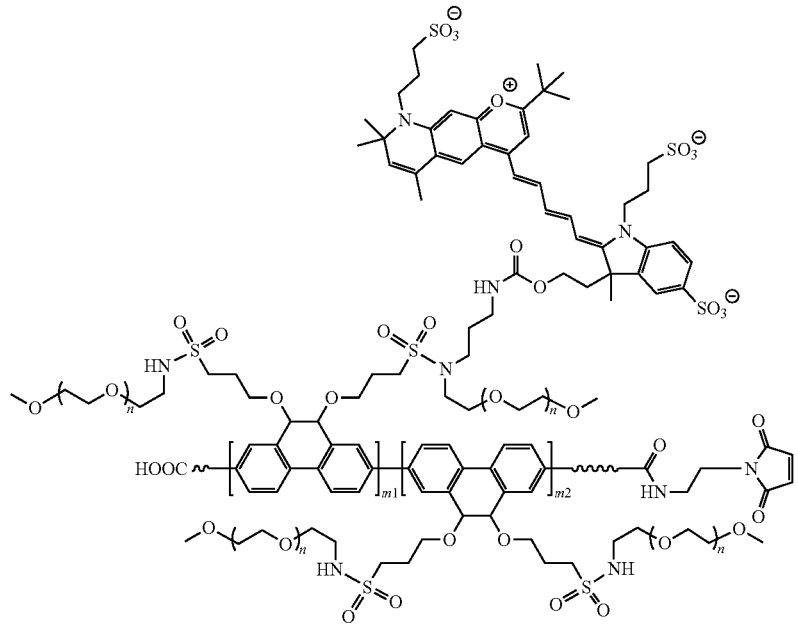
4
The reduced CD4 mAb is MES was mixed with polymer-maleimide (brought to RT before mixing) and incubated for 3 hours by rolling at RT, protected from light, to form conjugate (5). This unpurified conjugate can be stored overnight at 4° C.
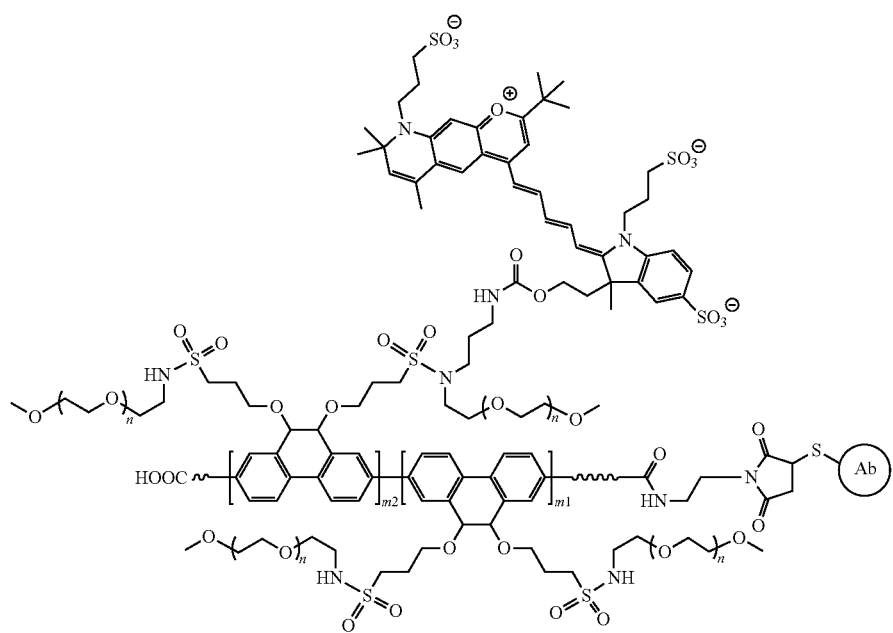
5

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A conjugated polymer according to Formula I:

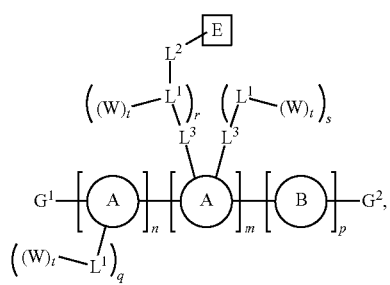

(I)

wherein:
each A is independently selected from the group consisting of an aromatic co-monomer and a heteroaromatic co-monomer;
$L^1$ comprises a sulfonamide, a sulfinamide, a disulfonamide, a disulfinamide, a sultam, an amide, a secondary amine, a phosphonamide, a phosphinamide, a phosphonamidate, a selenonamide, or a seleninamide; $L^2$ and $L^3$ are linker moieties;
W is a water-solubilizing moiety;
each E is an independently selected chromophore, functional moiety, or binding agent;
each B is independently selected from the group consisting of an aromatic co-monomer, a heteroaromatic co-monomer, a bandgap-modifying monomer, optionally substituted eth lene, and optionally substituted ethynylene;
$G^1$ and $G^2$ are independently selected from an unmodified polymer terminus and a modified polymer terminus, wherein one or both of $G^1$ and $G^2$ are modified with a capping moiety;
subscripts n and m are independently integers ranging from 1 to 10,000,
subscript p is an integer ranging from 0 to 10,000, and the sum of subscripts n, m, and p ranges from 2 to 10,000;
subscript q is 1, 2, 3, or 4;
subscript r is 1, 2, 3, or 4;
subscript s is 0, 1, 2, or 3;
subscript t is 1 or 2
the sum of subscript r and s ranges from 1 to 4; and
A and B are distributed randomly or non-randomly in the conjugated polymer, wherein the functional moiety is a biotin, digoxigenin, a peptide tag, an oligonucleotide, or a polynucleotide, and the binding agent is a molecule or complex of molecules capable of specific binding to a target analyte, wherein the binding agent is selected from the group consisting of protein, antibody, antibody fragment, carbohydrate, polysaccharide, oligonucleotide, polynucleotide, lipid, affinity ligand, and aptamer.

2. The conjugated polymer of claim 1, wherein $L^3$ is a bond.

3. The conjugated polymer of claim 1, wherein:
subscript q is equal to the sum of subscripts r and s,
subscript r is 1 or 2,
if subscript r is 1, then subscript s is 0 or 1, and
if subscript r is 2, then subscript s is 0.

4. The conjugated polymer of claim 1, having a structure according to Formula II:

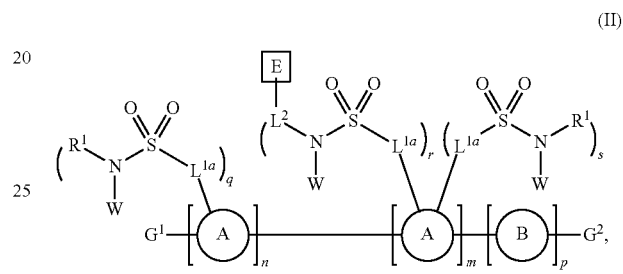

(II)

wherein:
$L^{1a}$ is a linker moiety; and
$R^1$ is selected from the group consisting of H and an amine protecting group.

5. The conjugated polymer of claim 4, wherein:
$L^{1a}$ is selected from the group consisting of a covalent bond, $C_{1-8}$ alkylene, 2- to 8-membered heteroalkylene, —NHC(O)$L^a$—, —C(O)NH$L^a$—, and —C(O)$L^a$—;
$L^2$ is selected from the group consisting of a covalent bond, $C_{1-8}$ alkylene; 2- to 8-membered heteroalkylene, —$L^b$NHC(O)—, —$L^b$C(O)NH—, —$L^b$C(O)—, —C(O)NH$L^b$—, and —C(O)$L^b$—; and
$L^a$ and $L^b$ are independently selected from the group consisting of $C_{1-8}$ alkylene and 2- to 8-membered heteroalkylene.

6. The conjugated polymer of claim 1, wherein W comprises one or more ethylene glycol monomers.

7. The conjugated polymer of claim 1, wherein W comprises poly(ethylene glycol).

8. The conjugated polymer of claim 1, wherein each A is the same co-monomer.

9. The conjugated polymer of claim 1, wherein A is a violet fluorescent monomer.

10. The conjugated polymer of claim 1, wherein A is a 9,10-phenanthrenedione-based monomer, a dihydrophenanthrene-based monomer, a dihydrophcnanthrene oxepine-based monomer, a fluorene-based monomer, or a fluorenooxepine-based monomer.

11. The conjugated polymer of claim 1, having a structure according to Formula III:

(III)

wherein each subscript t is an integer ranging from 1 to 20.

12. The conjugated polymer of claim 1, wherein one or both of $G^1$ and $G^2$ modified with a capping moiety is covalently bonded to a binding agent or a substrate material.

13. The conjugated polymer of claim 1, wherein one of $G^1$ and $G^2$ is modified with a capping moiety, and one of $G^1$ and $G^2$ is modified with reactive functional group.

14. The conjugated polymer of claim 1, wherein each E is an independently selected chromophore.

15. A method of making a conjugated polymer according to Formula II:

(II)

the method comprising converting a conjugated polymer according to Formula IIa:

(IIa)

to the polymer according to Formula II, wherein:

A is a fluorescent monomer;

$L^{1a}$ and $L^2$ are linker moieties;

W is a water-solubilizing moiety;

each E is an independently selected chromophore;

each B is independently selected from the group consisting of an aromatic co-monomer, a heteroaromatic co-monomer, a bandgap-modifying monomer, optionally substituted ethylene, and optionally substituted ethynylene;

$G^1$ and $G^2$ are independently selected from an unmodified polymer terminus and a modified polymer terminus, wherein one or both of $G^1$ and $G^2$ are modified with a capping moiety;

$R^1$ is selected from the group consisting of H and an amine protecting group;

subscripts n and in are independently integers ranging from 1 to 10,000, subscript p is an integer ranging from 0 to 10,000, and the sum of subscripts n, m, and p ranges from 2 to 10,000;

subscript q is 1, 2, 3, or 4;

subscript r is 1, 2, 3, or 4;

subscript s is 0, 1, 2, or 3;

subscript t is 1 or 2 the sum of subscript r and s ranges from 1 to 4; and

A and B are distributed randomly or non-randomly in the fluorescent polymer.

* * * * *